United States Patent [19]

Mondry

[11] Patent Number: 5,315,990
[45] Date of Patent: May 31, 1994

[54] METHOD FOR DELIVERING INCREMENTAL DOSES OF OXYGEN FOR MAXIMIZING BLOOD OXYGEN SATURATION LEVELS

[76] Inventor: Adolph J. Mondry, 46340 Concord Dr., Plymouth, Mich. 48170

[21] Appl. No.: 982,389

[22] Filed: Nov. 25, 1992

Related U.S. Application Data

[63] Continuation-in-part of Ser. No. 814,481, Dec. 30, 1991, abandoned.

[51] Int. Cl.$^5$ .............................. A62B 7/00; A62B 9/02
[52] U.S. Cl. ........................... 128/205.11; 128/205.24; 128/205.25; 128/205.26
[58] Field of Search ................. 128/204.22, 204.23, 128/204.18, 205.11, 205.24, 205.23, 205.26, 633, 634, 205.25

[56] References Cited

U.S. PATENT DOCUMENTS

| | | | |
|---|---|---|---|
| 3,734,091 | 5/1973 | Taplin | 128/204.23 |
| 4,121,578 | 10/1978 | Torzala | 128/204.23 |
| 4,326,513 | 4/1982 | Schulz et al. | 128/204.23 |
| 4,665,911 | 5/1987 | Williams et al. | 128/204.23 |
| 4,671,297 | 6/1987 | Schulze, Jr. | 128/204.23 |
| 4,932,402 | 6/1990 | Snook et al. | 128/204.23 |
| 4,972,842 | 11/1990 | Korten et al. | 128/200.24 |
| 4,986,268 | 1/1991 | Tehrani | 128/204.22 |
| 5,103,814 | 4/1992 | Maher | 128/204.23 |

OTHER PUBLICATIONS

"Closed-loop Control of SaO$_2$ in the Neonate", by Paul E. Morozoff, Ron W. Evans from Biomedical Instrumentation & Technology, Mar./Apr. 1992;26:117–123.

Primary Examiner—Edgar S. Burr
Assistant Examiner—Kimberly L. Asher
Attorney, Agent, or Firm—Brooks & Kushman

[57] ABSTRACT

Methods for automatically maximizing blood oxygenation saturation or maintaining blood oxygen saturation levels in adult patients having an oxygen requiring pulmonary disease and infant patients having underdeveloped lungs, within a specified range of values. In one embodiment, the method includes energizing a valve to deliver oxygen to the patient at a first rate and measuring the associated average oxygen saturation level of the patient. The method also includes deenergizing the valve and energizing another valve to deliver oxygen to the patient at a second rate and measuring the second average oxygen saturation level of the patient. A dominant valve, the valve associated with the higher average oxygen saturation level, is identified based on the measured oxygen saturation levels and then energized to deliver oxygen to the patient, thereby maximizing the blood oxygen saturation level in the patient.

3 Claims, 25 Drawing Sheets

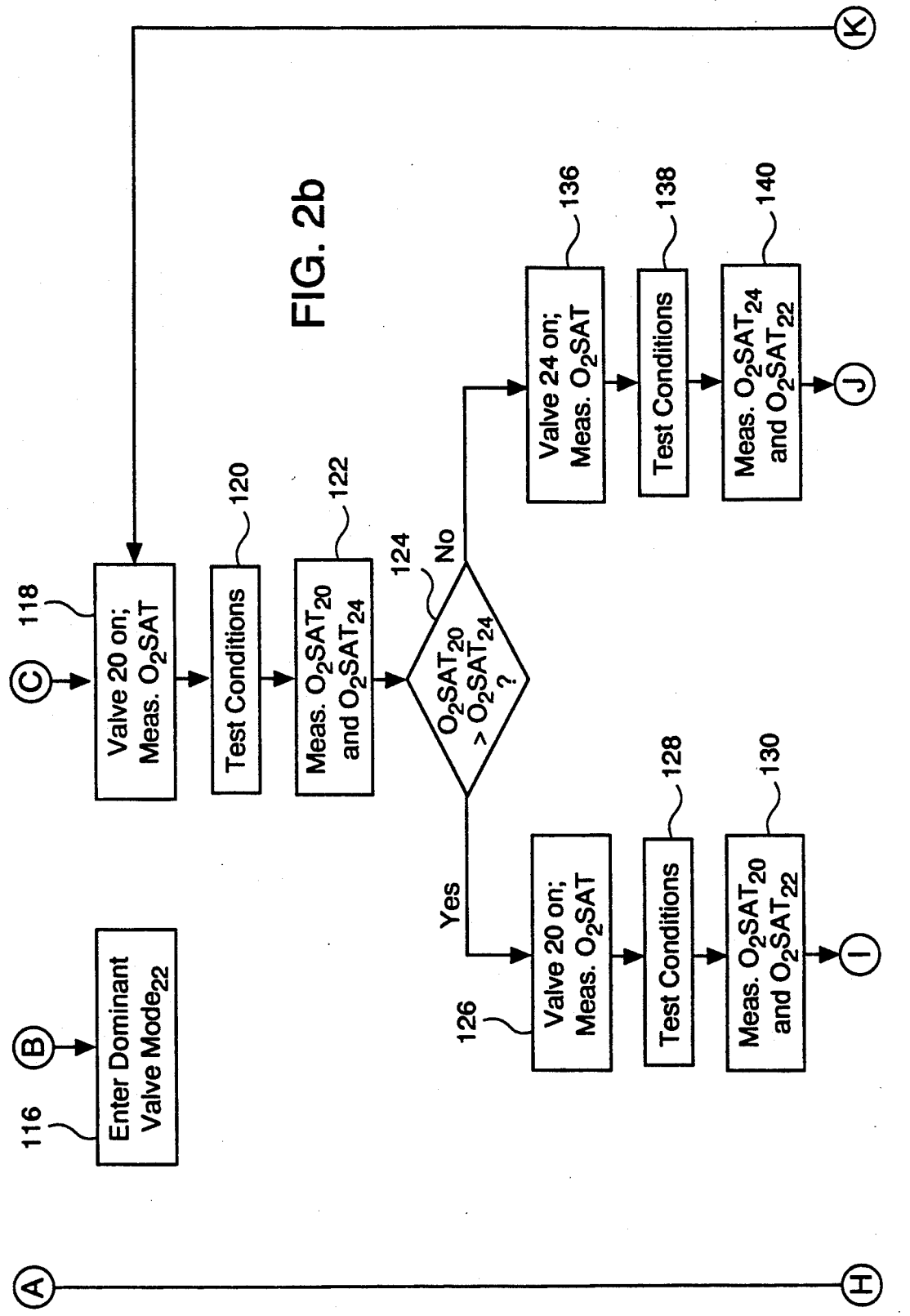

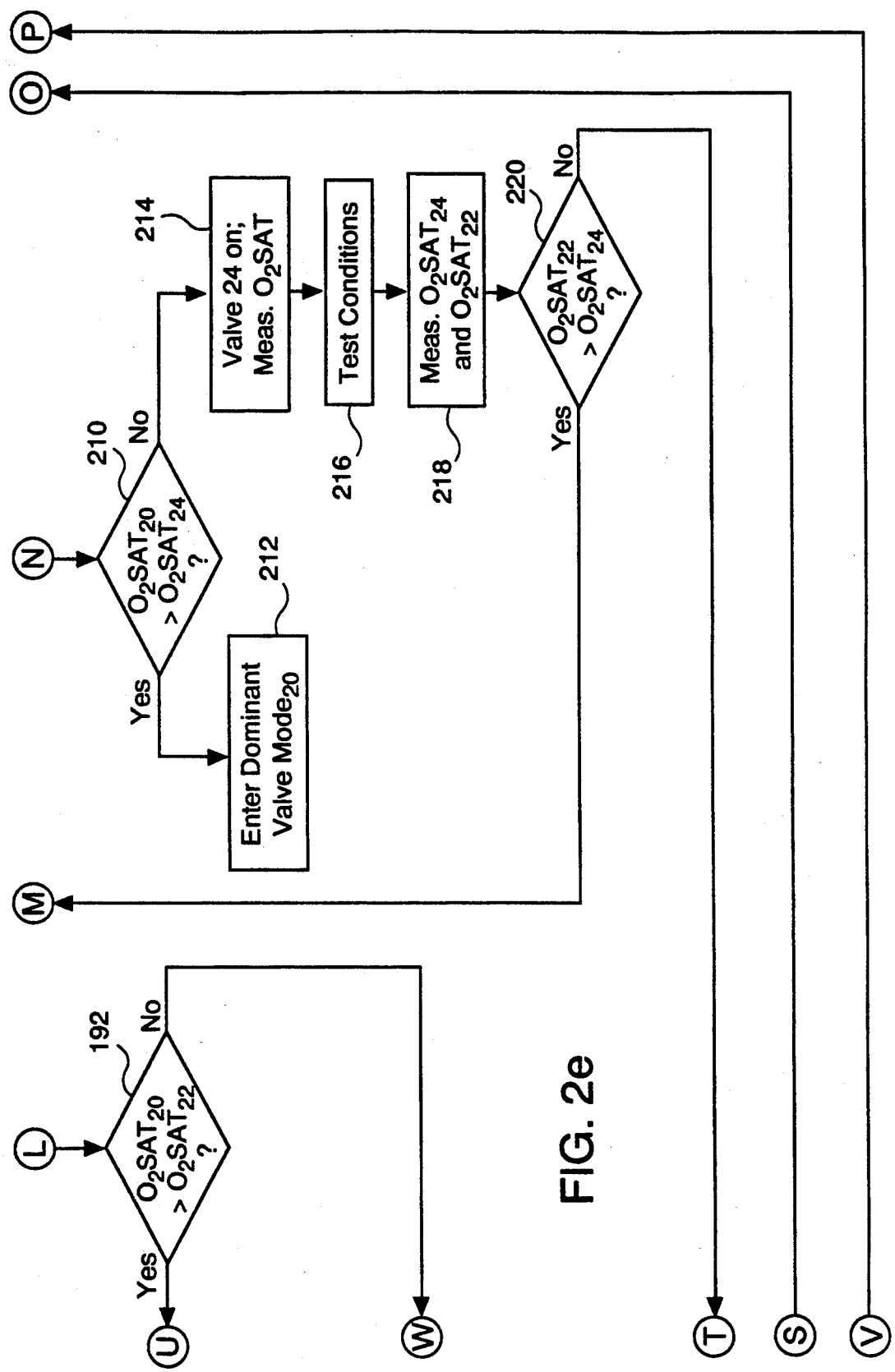

METHOD FOR DELIVERING INCREMENTAL DOSES OF OXYGEN FOR MAXIMIZING BLOOD OXYGEN SATURATION LEVELS

CROSS-REFERENCE TO RELATED APPLICATION

This application is a continuation-in-part of U.S. patent appliction Ser. No. 814,481, filed Dec. 30, 1991, now abandoned, and titled "Oxydosimeter", which is hereby expressly incorporated by reference in its entirety.

TECHNICAL FIELD

The present invention relates to an oxydosimeter, and, more particularly, to an oxydosimeter for automatically affecting the blood oxygen saturation level in patients having an obstructive pulmonary disease.

BACKGROUND ART

Oxydosimeters are used by physicians and therapists to treat patients having chronic obstructive pulmonary diseases (COPD), such as emphysema. Typically, COPD patients exhibit symptoms ranging from a hacking cough, to a continual shortness of breath. These symptoms are known to therapists and physicians to possibly reflect hypoxia, a term which refers to a deficiency of oxygen in the blood, oftentimes due to impaired respiratory conditions. In general, hypoxia is defined as an average, or mean, blood oxygen saturation level less than 90%.

Oxydosimeters are also used to treat infants, or neonates, born with underdeveloped lungs. It is well known that neonates must be adequately oxygenated in order to avoid organ damage or, in the worst case, death. Frequently, clinical manifestations of neonatal hypoxia are subtle, although its effects may be rather severe later in life. For example, children who were hypoxic as neonates may suffer mental retardation from the lack of oxygen supplied to their body by their undeveloped lungs. On the other hand, care should be exercised to avoid delivering excessive oxygen, which may lead to retinal damage in young children.

A microprocessor-based device for treating neonates is disclosed in the article titled "Closed-loop Control of SaO$_2$ in the Neonate," authored by Paul E. Morozoff and Ron W. Evans and published in the March/April 1992 issue of Biomedical Instrumentation and Technology. This device is used to maintain a preset oxygen saturation level in neonates so that the maximum amount of oxygen is delivered to the body. The system comprises a pulse oximeter utilized to gather patient data, a microprocessor to analyze the data and control the machine, and a motorized air-oxygen blender to provide the correct oxygen saturation level to the neonate. This device controls a mechanical valve separate from the mixer valves with servo-motors and potentiometers. With this device, however, a one-to-one mechanical-electrical correspondence is impossible. As a result, operators must frequently make manual adjustments to the device to maintain the desired blood oxygen saturation level of the patient.

It is, however, desirable to provide an improved method and apparatus for automatically maintaining the blood oxygen saturation level within desired ranges in neonates and to maximize the blood oxygen saturation level in adult COPD patients.

SUMMARY OF THE INVENTION

It is an object of the present invention to provide a method and apparatus for automatically maintaining blood oxygen saturation levels in adult and infant patients suffering from an obstructive pulmonary disease or underdeveloped lungs, respectively.

It is a further object of the present invention to provide a method and apparatus for maximizing the blood oxygen saturation level in adult patients with an obstructive pulmonary disease.

In carrying out the above objects, and other objects and features of the present invention, a method is provided for delivering incremental doses of oxygen to a patient having an obstructive pulmonary disease to maximize the blood oxygen saturation level in the patient. The method comprises (a) energizing one of a plurality of valves to deliver the incremental doses of oxygen to the patient at a first rate, and (b) measuring an associated average oxygen saturation level of the patient to obtain a first average oxygen saturation signal. The method also comprises (c) deenergizing the one valve and energizing another valve to deliver the incremental doses of oxygen to the patient at a second rate, and (d) measuring a second associated average oxygen saturation level of the patient to obtain a second average oxygen saturation signal. The method also comprises (e) identifying a dominant valve based on the first average oxygen saturation signal and the second average oxygen saturation signal, the dominant valve being the valve associated with the higher oxygen saturation level in the patient, and (f) energizing the dominant valve, thereby delivering the incremental doses of oxygen to the patient to maximize the blood oxygen saturation level in the patient.

Methods are also provided for maintaining the mean blood oxygen saturation level of a patient within predetermined desired mean blood oxygen saturation levels. Systems are also provided for carrying the methods.

The advantages accruing to the present invention are numerous. For example, the oxydosimeters of the present invention automatically deliver incremental metered doses of oxygen to the patient based on average or mean blood oxygen saturation, with a high probability of increasing patient comfort, decreasing right-sided heart strain and failure, and increasing life span. Additionally, the oxydosimeters of the present invention are portable, allowing treatment of patients outside of the traditional hospital setting. Still further, the present invention may reduce oxygen consumption and operates without the need for continual manual adjustments, thereby reducing the amount of nursing care required and, therefore, lowering medical costs.

The above objects and other objects, features, and advantages of the present invention will be readily appreciated by one of ordinary skill in the art from the following detailed description of the best mode for carrying out the invention, when taken in connection with the accompanying drawings.

BRIEF DESCRIPTION OF DRAWINGS

FIGS. 2a-2f are a flowchart detailing the oxygenation strategy of the present invention for use with the adult COPD oxydosimeter shown in FIG. 1;

BEST MODE FOR CARRYING OUT THE INVENTION

Adult COPD Oxydosimeter

Figure 1:
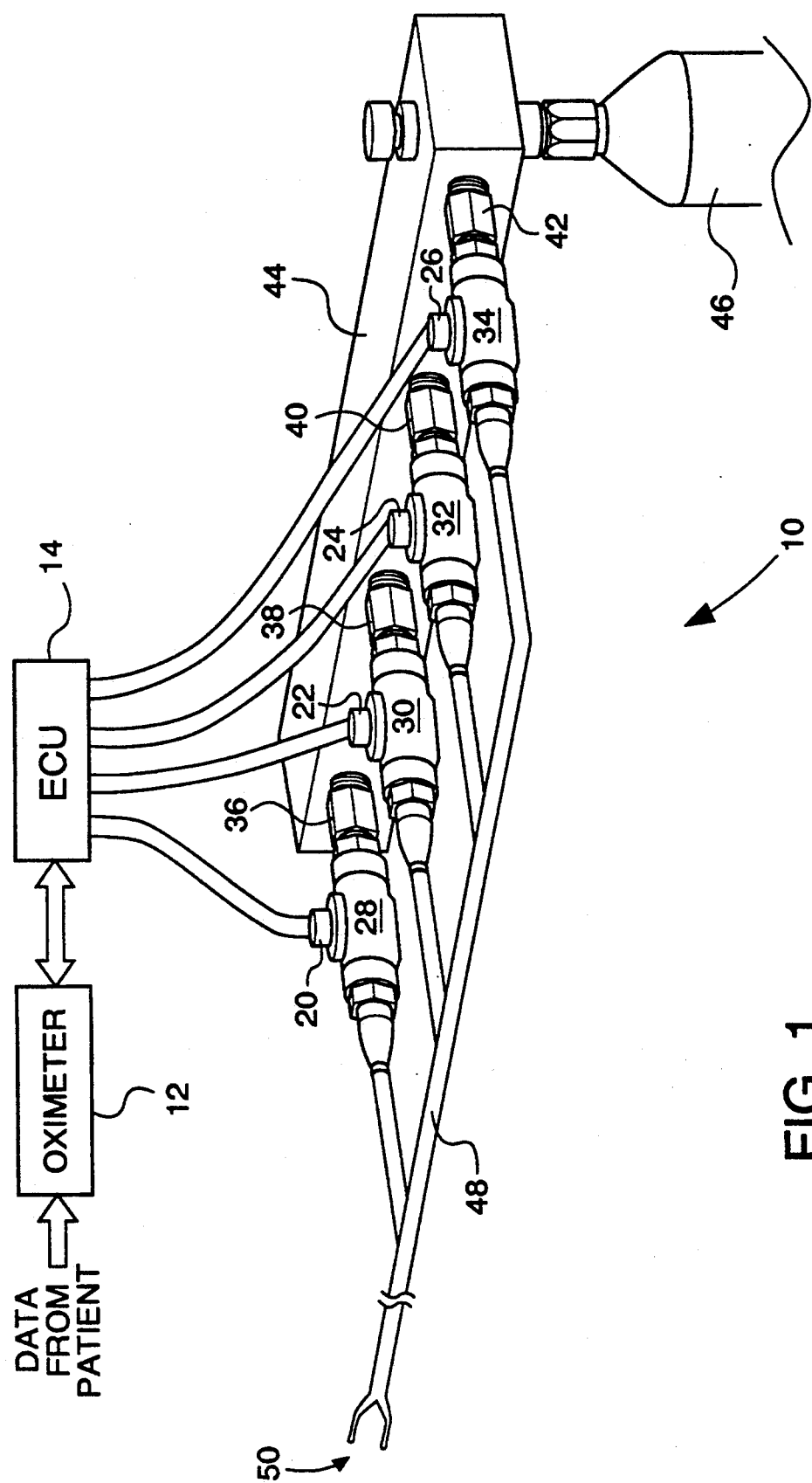
FIG. 1 is a perspective view of a first oxydosimeter embodiment of the present invention, for use as an adult COPD oxydosimeter.

Referring now to FIG. 1, there is illustrated the first preferred embodiment of the oxydosimeter system of the present invention, for use as an adult COPD oxydosimeter, shown generally by reference numeral 10. As shown, the system 10 includes a pulse oximeter 12 which is preferably connected to a patient (not specifically illustrated) via the patient's finger. The pulse oximeter 12 may be any of those commercially available, such as Model N100C/D/E/F manufactured by Nellcor, Inc., of Haywood, Calif., United States of America, or may be application specific. The pulse oximeter 12 measures both the pulse rate and the oxygen saturation of the patient. As is known, the pulse oximeter 12 works by measuring the amount of light absorbed through the skin, and correlates the measured data to pulse rate and oxygen saturation data standards. The pulse rate and oxygen saturation level data are then transferred to a microprocessor-based electronic control unit (ECU) 14. The ECU 14 preferably operates on power delivered from either an AC or DC power supply, lending portability to the oxydosimeter system 10 out of the typical hospital environment. The ECU 14 executes a control strategy, processing and analyzing the patient data to determine the proper amount of oxygen to deliver to the patient, as described in greater detail herein below.

With continuing reference to FIG. 1, the ECU 14 is in electrical communication with and controls a plurality of solenoid valves 20, 22, 24 and 26, such as the variably opening valve described in U.S. Pat. No. 5,008,773. The oxygen regulator-flowmeters 36, 38, 40 and 42, such as Model HMG-5SN commercially available from Thermodyne Industries, St. Louis, Mo., United States of America, are shown modified to include a plurality of solenoid valves which are connected to four adapters 28, 30, 32 and 34. The flowmeters and the adapters could be fabricated into a single unit. The regulator-flowmeters preferably test at one, two, three and four liters per minute (L/min) oxygen flow, respectively. As shown, one end of each regulator-flowmeter is preferably connected to a high pressure oxygen manifold 44, which is preferably in fluid communication with an oxygen source shown generally by reference numeral 46.

Each regulator-flowmeter delivers oxygen to the solenoid valves 20, 22, 24 and 26. Oxygen tubing, shown generally by reference numeral 48, extends from the solenoid valves and is distally fused into a single tube which is connected to nasal prongs 50. The nasal prongs 50, which preferably connect to the patient via the patient's nostrils, deliver oxygen to the patient at a varying rate (e.g. from 1 L/min to 4 L/min, in 1 L/min increments), as determined by the ECU 14.

The oxydosimeter system 10 may also be adapted for use with a simple aerosol mask (not specifically illustrated), which is utilized in place of the nasal prongs. The aerosol mask allows poorly humidified oxygen to flow at three, five, seven and nine L/min, respectively, through each of the regulator-flowmeters 36, 38, 40 and 42 of FIG. 1. The plastic oxygen tubing 48 preferably connects to four venturi valves set at 24%, 28%, 32% and 36% oxygen concentrations—all of which are connected to an aerosol mask.

It should be appreciated that any oxygen delivery system using standard nasal prongs may be converted into a fully automated oxydosimeter like the oxydosimeter 10. The flowmeter outlet of the standard oxygen delivery system is connected to a variably opening solenoid valve with a Coulomb controlling circuit, such as that disclosed in the '773 patent, by oxygen tubing. Oxygen tubing connects the valve, which is connected to the ECU, to the nasal prongs and the patient.

Figure 2A:
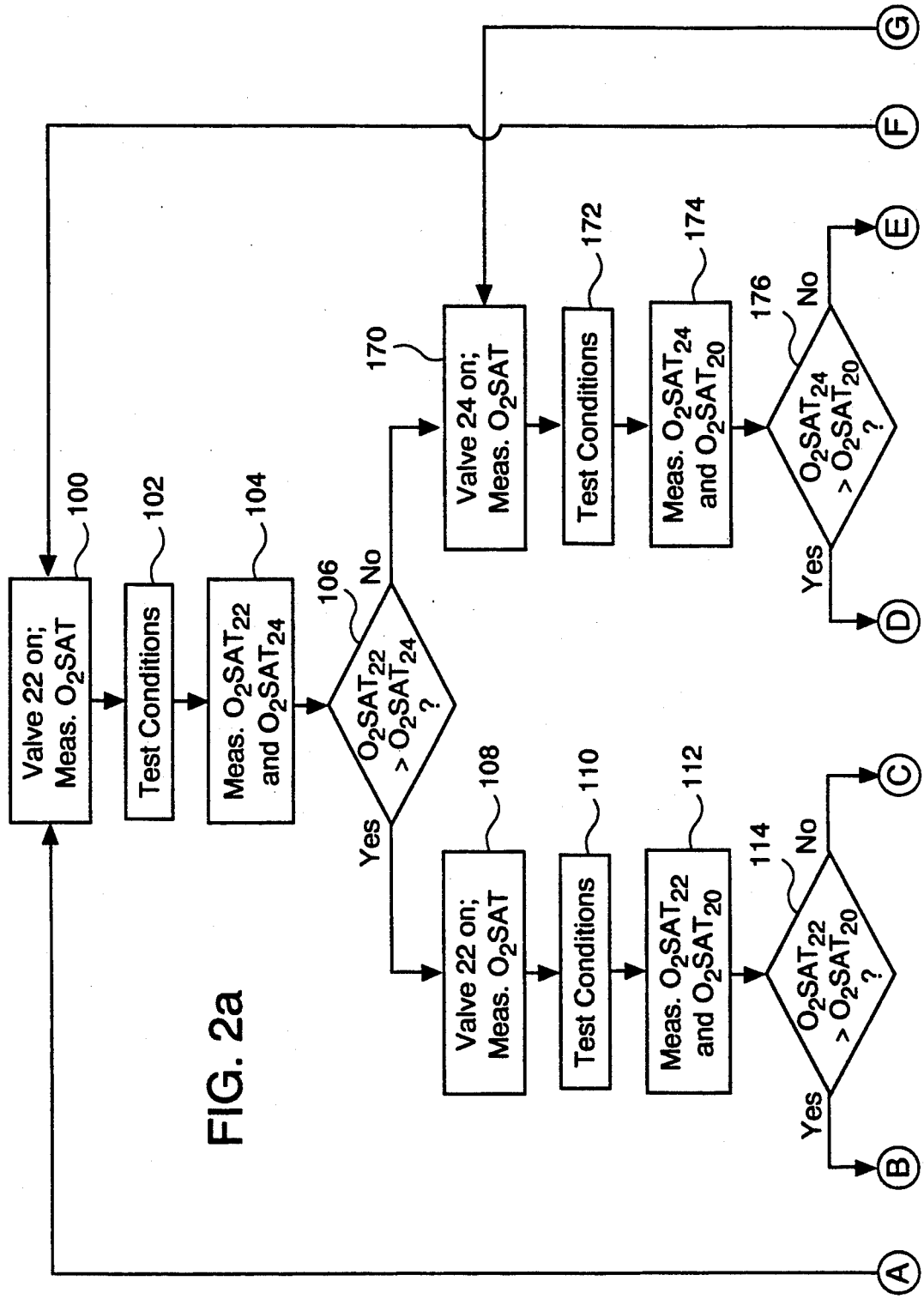
Figure 2C:
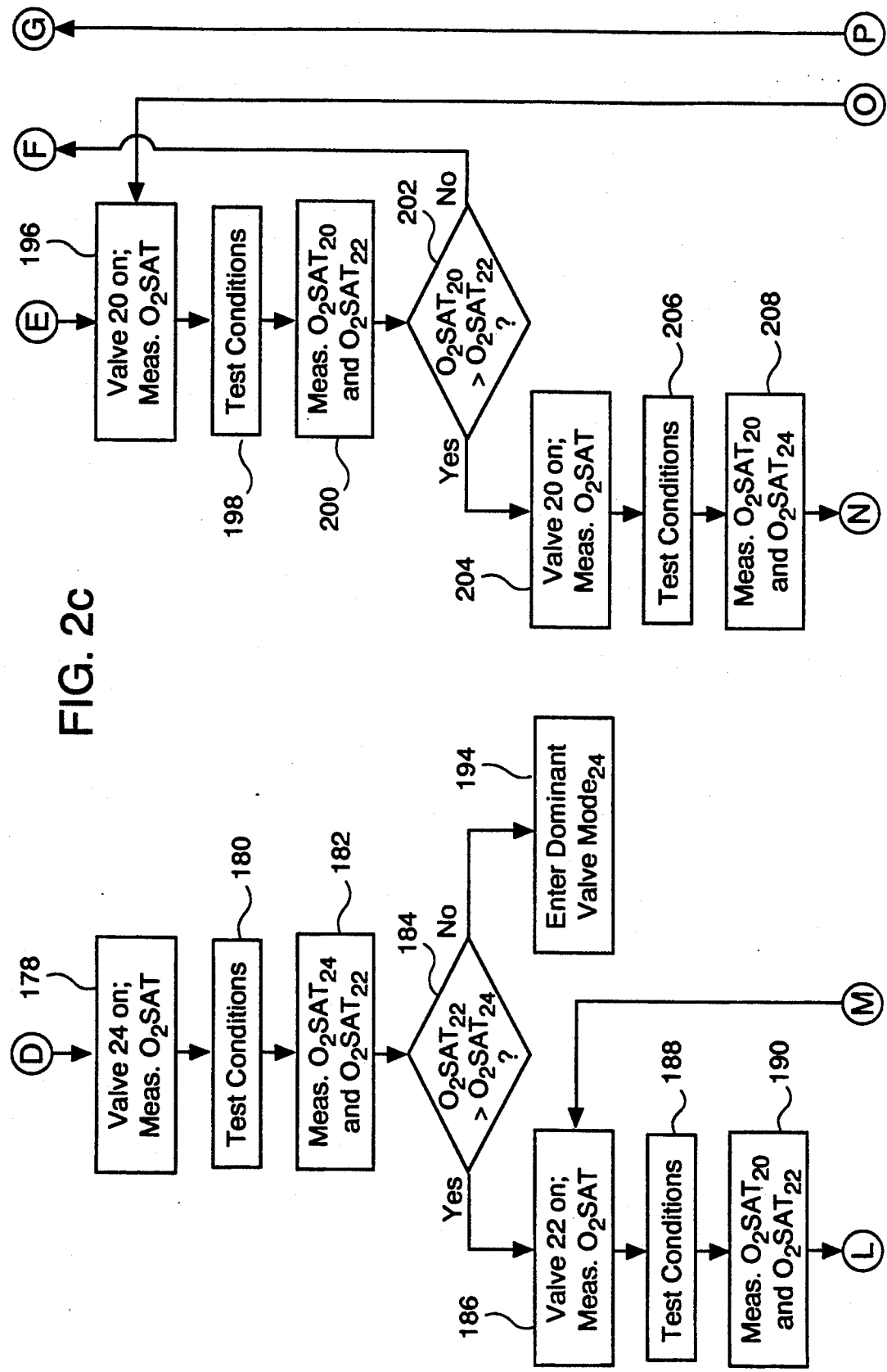
Figure 2D:
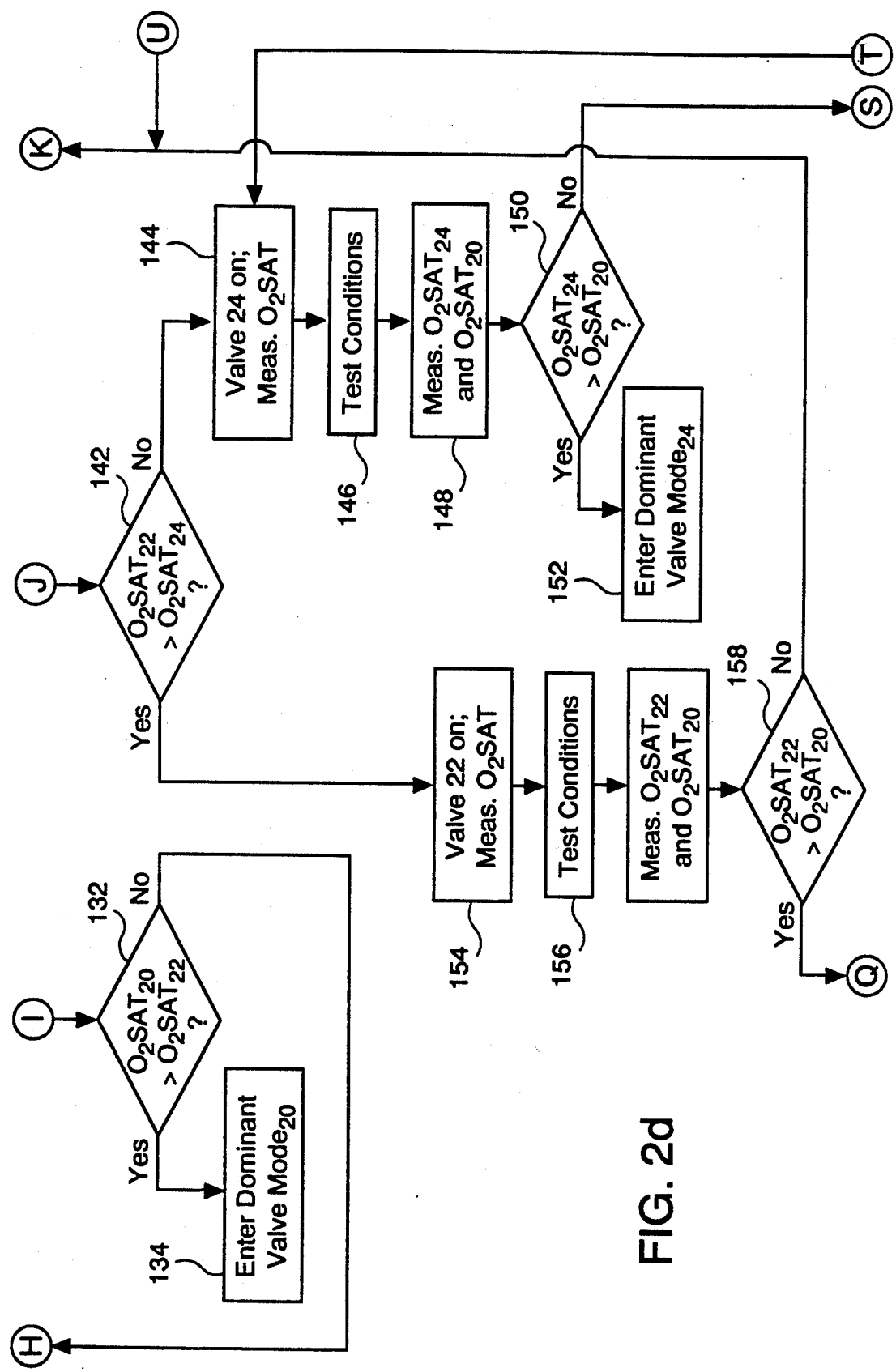
Figure 2F:
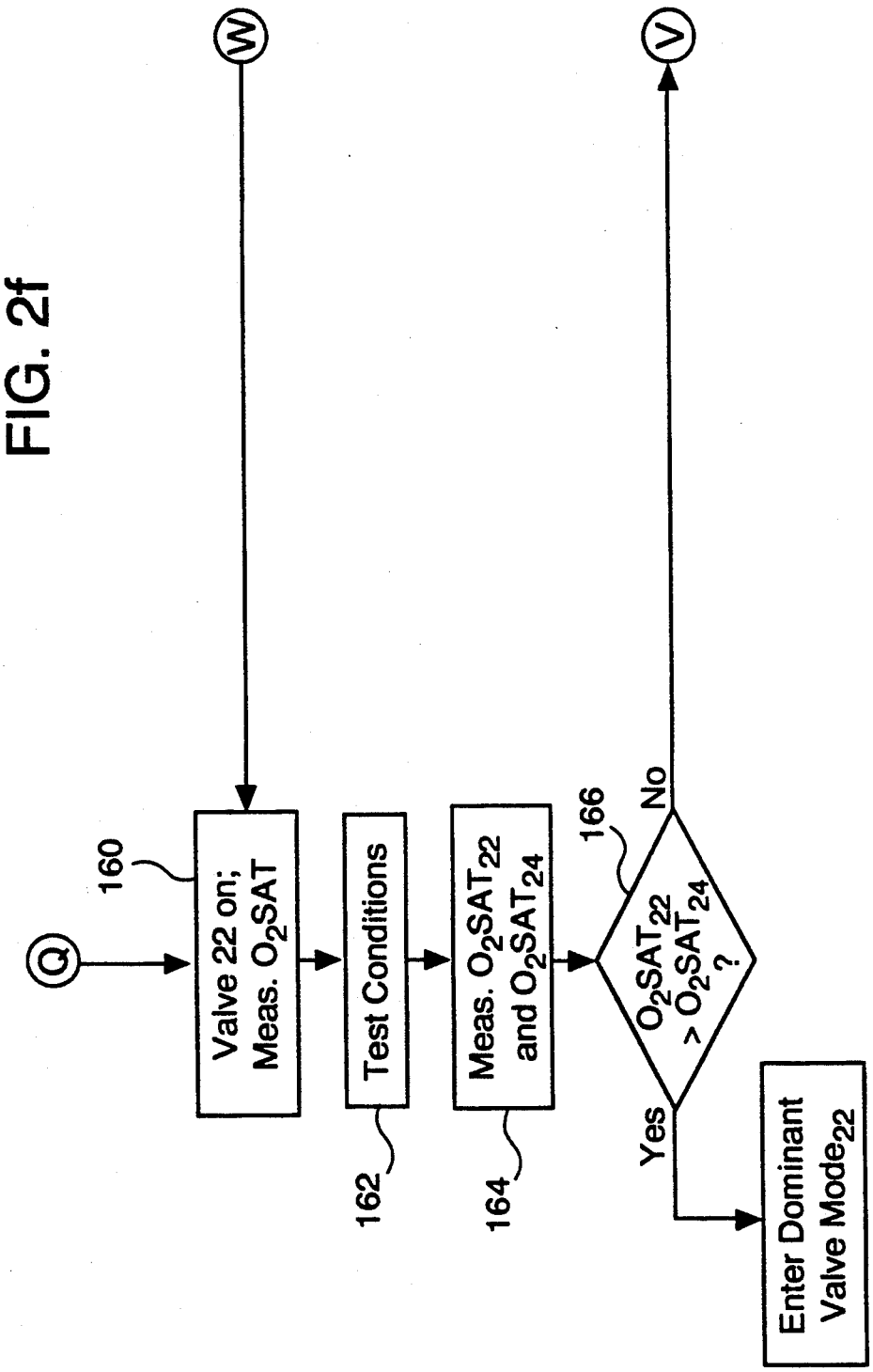

Referring now to FIGS. 2a–2f, there is shown a flowchart detailing the oxygenation strategy of the present invention for use with the adult COPD oxydosimeter 10 shown in FIG. 1. Generally, the strategy compares average oxygen saturation levels associated with the valves 20, 22, 24 and 26 to determine the dominant valve—the valve which delivers oxygen to the patient to obtain the highest oxygen saturation level. The duration of each state shown is thirty seconds. As best shown in FIG. 2a, at step 100 the ECU energizes only valve 22, which is the dominant solenoid valve at that point, and measures $O_2SAT_{22}$ and $PRATE_{22}$ over a period of sixty seconds, the present average oxygen saturation and pulse rate associated with valve 22. These oxygen saturation and pulse rate values are then compared with the previous thirty (30) oxygen saturation and pulse rate values, which are stored in the memory of the ECU. If the present values of $O_2SAT_{22}$ and $PRATE_{22}$ are the highest, those values become the baseline values and valve 22 becomes the baseline valve for oxygen saturation and pulse rate. It should be appreciated that there could be one baseline valve for oxygen saturation and a different baseline valve for pulse rate. If the present values are not the highest, the highest values becomes the baseline values.

Figure 3:
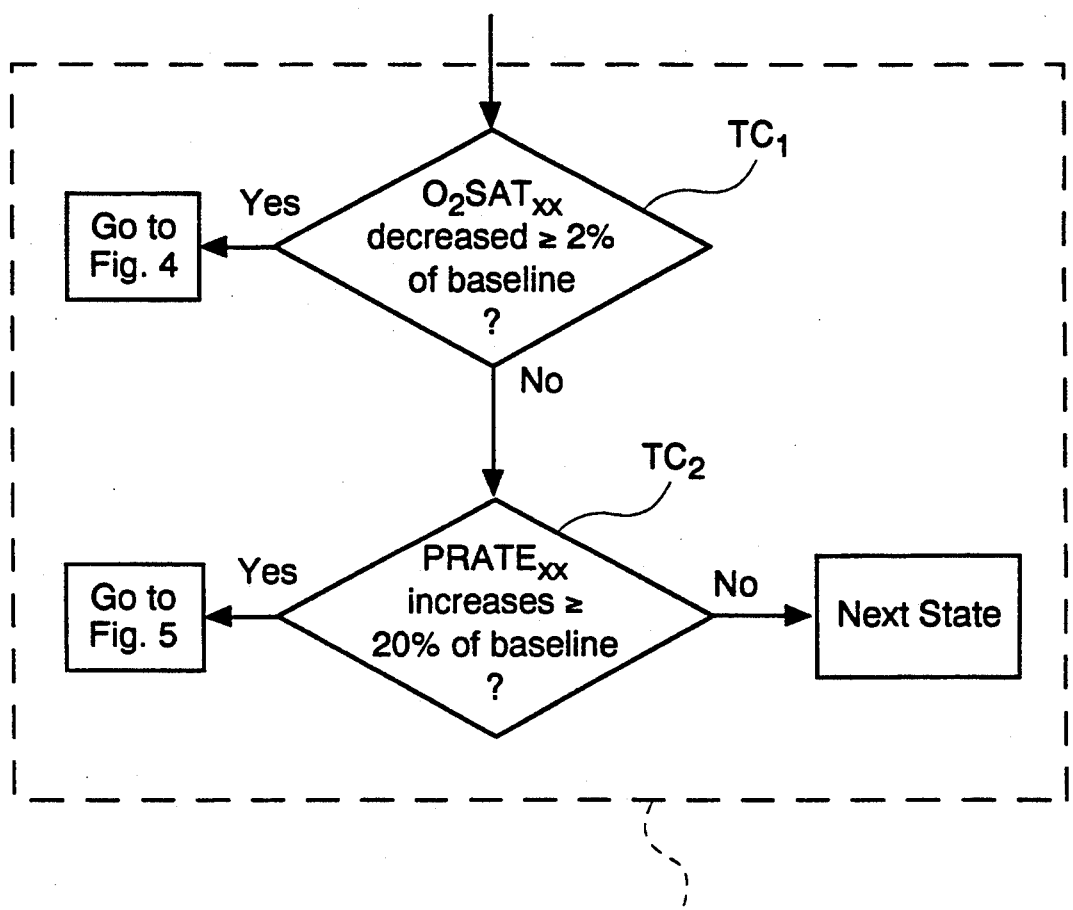
FIG. 3 is a detail of the Test Conditions box shown in FIG. 2, utilized by the present invention to determine entry into the Oxygen Saturation Exercise Mode and the Pulse Rate Exercise Mode.

With continuing reference to FIG. 2a, at step 102 a Test Conditions step is performed by the ECU. In the preferred embodiment, the Test Conditions step 102 actually consists of two steps, which are shown in greater detail in FIG. 3. Step 102 is applied to step 100 about every 5 seconds for the entire sixty second duration of the step 100. It should be noted that the step 100/step 102 combination is actually preferably a predetermined number of times prior to step 100. For example, step 100 could represent eleven (11) test conditions and twelve (12) sub-states. For ease of illustration and the sake of clarity, however, only one pair is actually illustrated. It should also be noted that the same representation could be utilized for each state in FIGS. 2a-2f and FIGS. 6-8. As best shown in FIG. 3, at step TC (wherein XX=22), the ECU determines whether average $O_2SAT_{22}$ has decreased by an amount greater than or equal to about 2% of baseline oxygen saturation. If it has, control flow jumps to the Oxygen Saturation Exercise Mode, best shown in FIG. 4.

Figure 4:
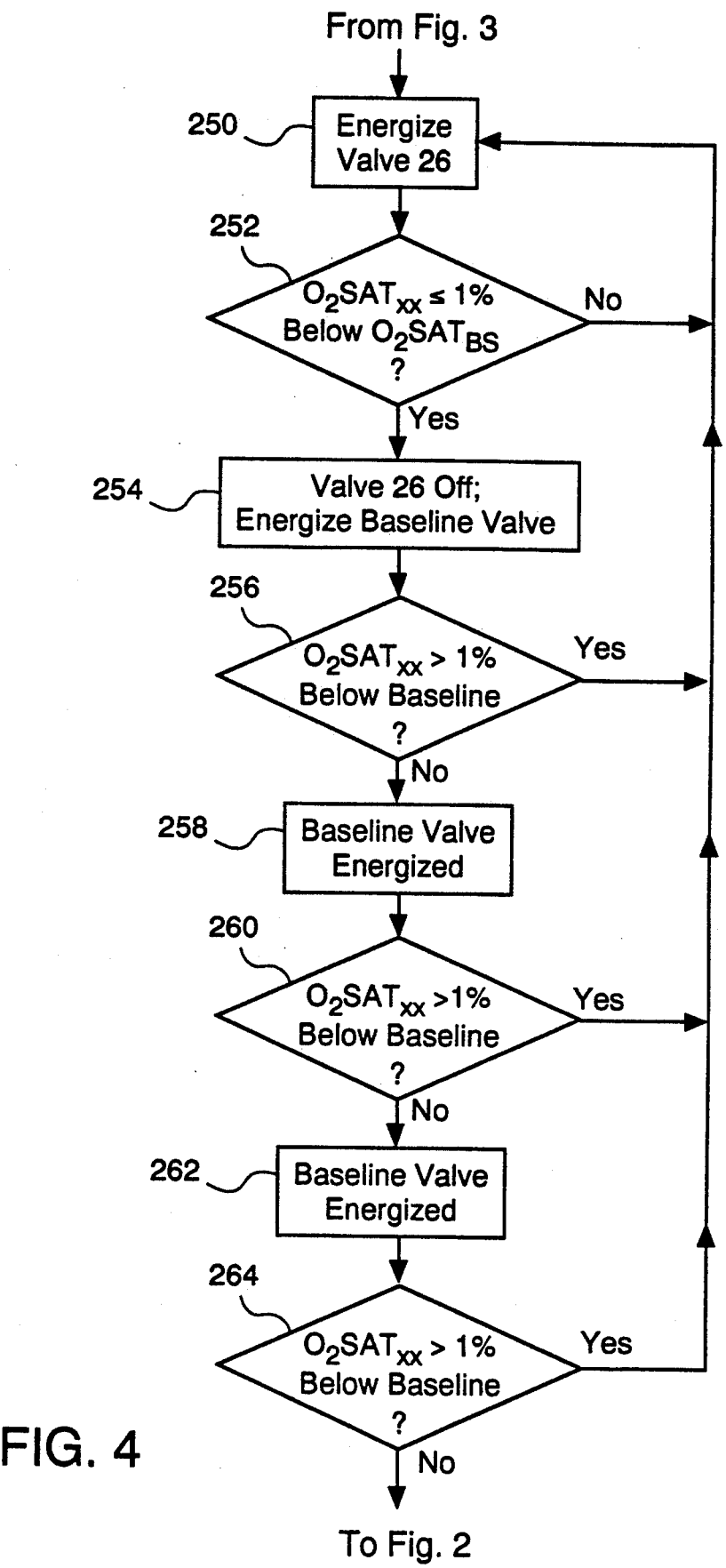
FIG. 4 is a flowchart detailing the Oxygen Saturation Exercise Mode of the oxygenation strategy of the present invention.

Referring now to FIG. 4, at step 250 of the Oxygen Saturation Exercise Mode, the ECU increases the amount of oxygen delivered to the patient by energizing valve 26, the 4 L/min valve. At step 252, the ECU measures $O_2SAT_{26}$ and determines Whether the average oxygen saturation has increased to a value less than or equal to about 1% below the baseline oxygen saturation. If it has not, the patient continues to receives oxygen at a rate of 4 L/min. If the average oxygen saturation has so increased, at step 254 the ECU deenergizes the valve 26 and energizes the baseline valve, which delivers oxygen at a lower rate. At steps 256-264, this process is repeated to ensure maximal oxygenation.

Referring once again to FIG. 3, if the condition of step $TC_1$ is not satisfied, at step $TC_2$ (wherein XX=22 at this point) the ECU determines whether $PRATE_{22}$ has increased by an amount greater than or equal to about 20% of the baseline pulse rate. If the pulse rate condition is not satisfied, control flow returns to step 104 of FIG. 2a. If it has, control flow jumps to the Pulse Rate Exercise Mode, shown in FIG. 5.

Figure 5:
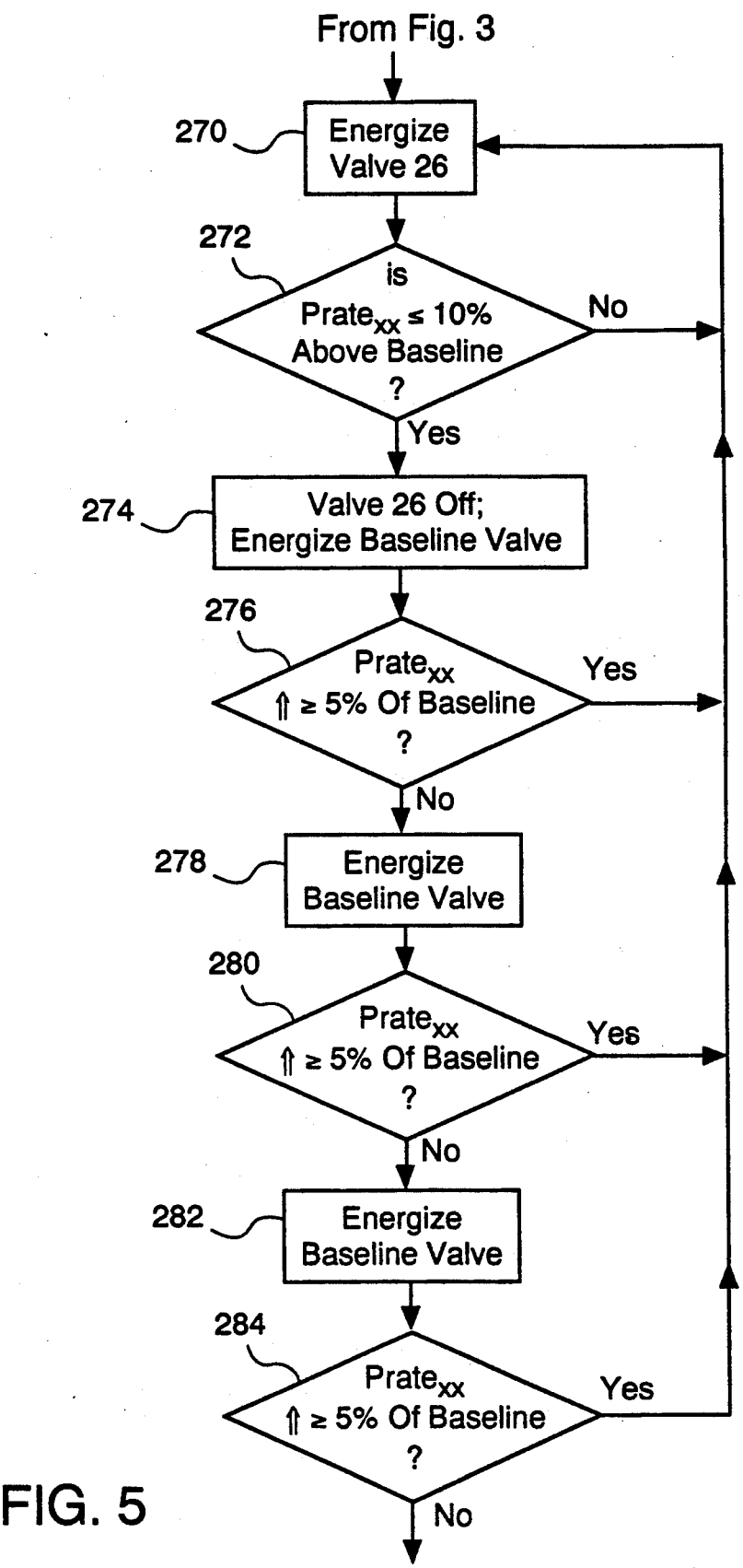
FIG. 5 is a flowchart detailing the Pulse Rate Exercise Mode of the oxygenation strategy of the present invention.

With reference to FIG. 5, at step 270 of the Pulse Rate Exercise Mode, the ECU increases the amount of oxygen delivered to the patient by energizing valve 26. At step 272, the ECU measures $PRATE_{26}$ and determines whether the patient's average pulse rate has decreased to a value that is less than or equal to about 10% above the baseline pulse rate. If it has not, the patient continues to receive oxygen at a rate of 4 L/min, in an attempt to lower the average pulse rate. If the pulse rate has so decreased, at step 274 the ECU deenergizes the valve 26 and energizes the baseline valve, which delivers oxygen at a lower rate. At step 276, the ECU determines whether the average pulse rate increases, due to the change in oxygen delivery, by an amount that is greater than or equal to about 5% of the baseline pulse rate ($PRATE_{BS}$). If it has, the baseline valve is deenergized and valve 26 is energized to once again lower the pulse rate. If the pulse rate has not increased when the baseline valve was energized, at step 278 the ECU maintains energization of the baseline valve. At steps 280-284, this process is repeated to insure maximal oxygenation.

With continuing reference to FIG. 2, at step 104 the ECU again measures average $O_2SAT_{22}$, but over a thirty second period. The ECU then deenergizes valve 22 and energizes valve 24. Thirty seconds later, the ECU measures $O_2SAT_{24}$, the average oxygen saturation in the patient associated with operation of the valve 24. At step 106, the ECU compares these measured oxygen saturations. If $O_2SAT_{22} > O_2SAT_{24}$, valve 22 remains the dominant valve. The ECU energizes valve 22 and deenergizes valve 24 and control flow jumps to step 108-114, wherein the process defined by steps 100-106 are repeated to determine dominance between valve 22 and valve 20 based on the average oxygen saturations associated with the valves.

With continuing reference to FIG. 2a, at step 108 valve 22 is energized and after sixty seconds the ECU measures average $O_2SAT_{22}$ and $PRATT_{22}$. The ECU then compares the present $O_2SAT_{22}$ and $PRATE_{22}$ to the previous thirty oxygen saturations and pulse rates. If the present $O_2SAT_{22}$ and $PRATE_{22}$ values are the highest, the present values become the baseline values. If the present values are not the highest, the highest values become the baseline values. At step 110, the ECU performs the Test Conditions (previously described and shown in FIG. 3, wherein XX=22). Preferably, one test condition is repeated every five (5) seconds as described. If the condition of step $TC_1$ of FIG. 3 is satisfied, the Oxygen Saturation Exercise Mode is carried out, as shown in FIG. 4 and described in greater detail above. If the condition of step $TC_2$ of FIG. 3 is satisfied, the Pulse Rate Exercise Mode is carried out, as shown in FIG. 5 and described in greater detail above. If none of the twelve test conditions at steps $TC_1$ and $TC_2$ are satisfied, control flow returns to step 112 of FIG. 2a.

With continuing reference to FIG. 2a, at step 112 the ECU first measures the present oxygen saturation associated with valve 22 over a thirty second period. The ECU then deenergizes valve 22, energizes valve 20, and measures the average oxygen saturation associated with valve 20 ($O_2SAT_{20}$) after thirty seconds. At step 114, the ECU determines whether the present $O_2SAT_{22}$ is greater than the present $O_2SAT_{20}$. If it is, valve 22 remains the dominant valve. Since valve 22 is the dominant valve for three consecutive intervals, valve 22 has complete dominance and the Dominant Valve Mode is entered at step 116, as shown in FIG. 2b.

Figure 6:
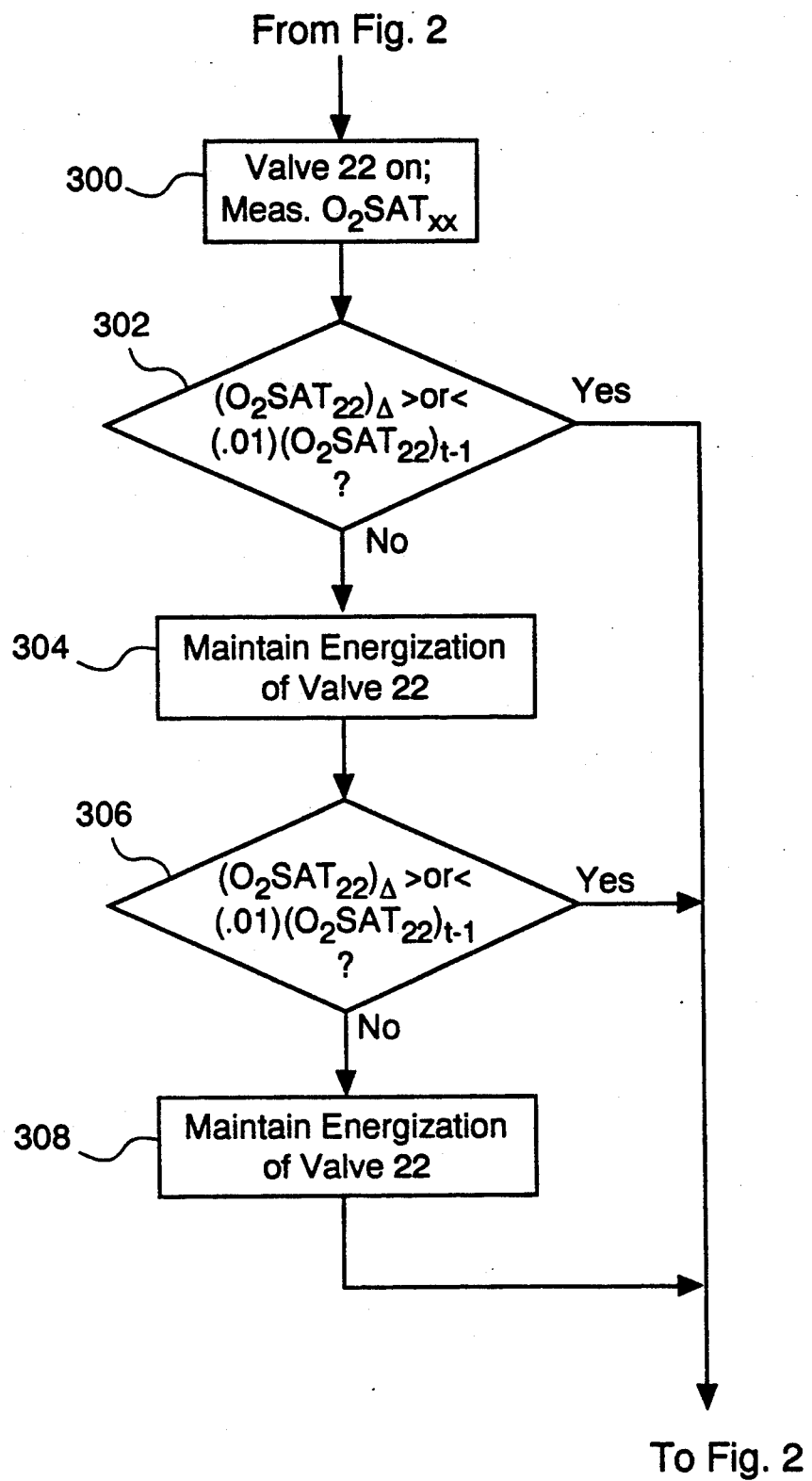
FIG. 6 is a flowchart detailing the Dominant Valve Mode oxygenation strategy utilized by the present invention when valve 22 of FIG. 2 is completely dominant.

Referring now to FIG. 6, there is shown a flowchart detailing the Dominant Valve Mode of the oxygenation strategy of the present invention. During this mode, the ECU monitors the oxygen saturation level at thirty second intervals as the patient receives oxygen from the dominant valve (i.e. valve 22). If the oxygen saturation level changes by more than a predetermined amount between intervals, Dominant Valve Mode$_{22}$ is exited and control returns to FIG. 2.

As shown in FIG. 6, the first step of the Dominant Valve Mode is to energize the dominant valve and begin measuring average oxygen saturation levels ($O_2SAT_{22}$) at thirty second intervals. At step 302, the ECU determines whether $(O_2SAT_{22})_A$, which represents the difference between the present oxygen saturation level, $(O_2SAT_{22})_t$, and the previous oxygen saturation level, $(O_2SAT_{22})_{t-1}$, is greater than or less about 1% of the previous $(O_2SAT_{22})_{t-1}$. Thus, the ECU is monitoring for a certain degree of change in the average oxygen saturation level. If the average oxygen saturation level has so changed over a thirty (30) second period, control flow jumps back to FIGS. 2a-2f for a determination of valve dominance as previously described. If the oxygen saturation level has not changed by the requisite amount, at step 304 the ECU maintains energization of valve 22 for a predetermined number of consecutive thirty (30) second intervals. In the preferred embodiment, valve 22 remains energized for twenty (20) intervals (i.e. about 10 minutes). Thereafter, at step 306, the ECU again determines whether $(O_2SAT_{22})_A$ is greater than or less about 1% of $(O_2SAT_{22})_{t-1}$. If the oxygen saturation level has so changed, control flow jumps back to step 100 of FIG. 2 for a determination of valve dominance as described in greater detail above. If the oxygen saturation level has not changed by the requisite amount, at step 308 the ECU maintains energization of valve 22 and measures oxygen saturation after a thirty second period, prior to returning to FIG. 2 at step 100 for a determination of valve dominance as described in greater detail above. At step 300, 304 and 308, every five seconds for thirty seconds per step, the ECU performs the Test Condition of FIG. 3. If the condition is satisfied, the Oxygen Saturation Exercise Mode of FIG. 4 is executed, as described in greater detail above. If the condition of step $TC_2$ is satisfied, the Pulse Rate Exercise Mode of FIG. 5 is executed. If neither of the test conditions are satisfied, control jumps back to step 100, 118 or 170 of FIGS. 2a-2f.

Figure 7:
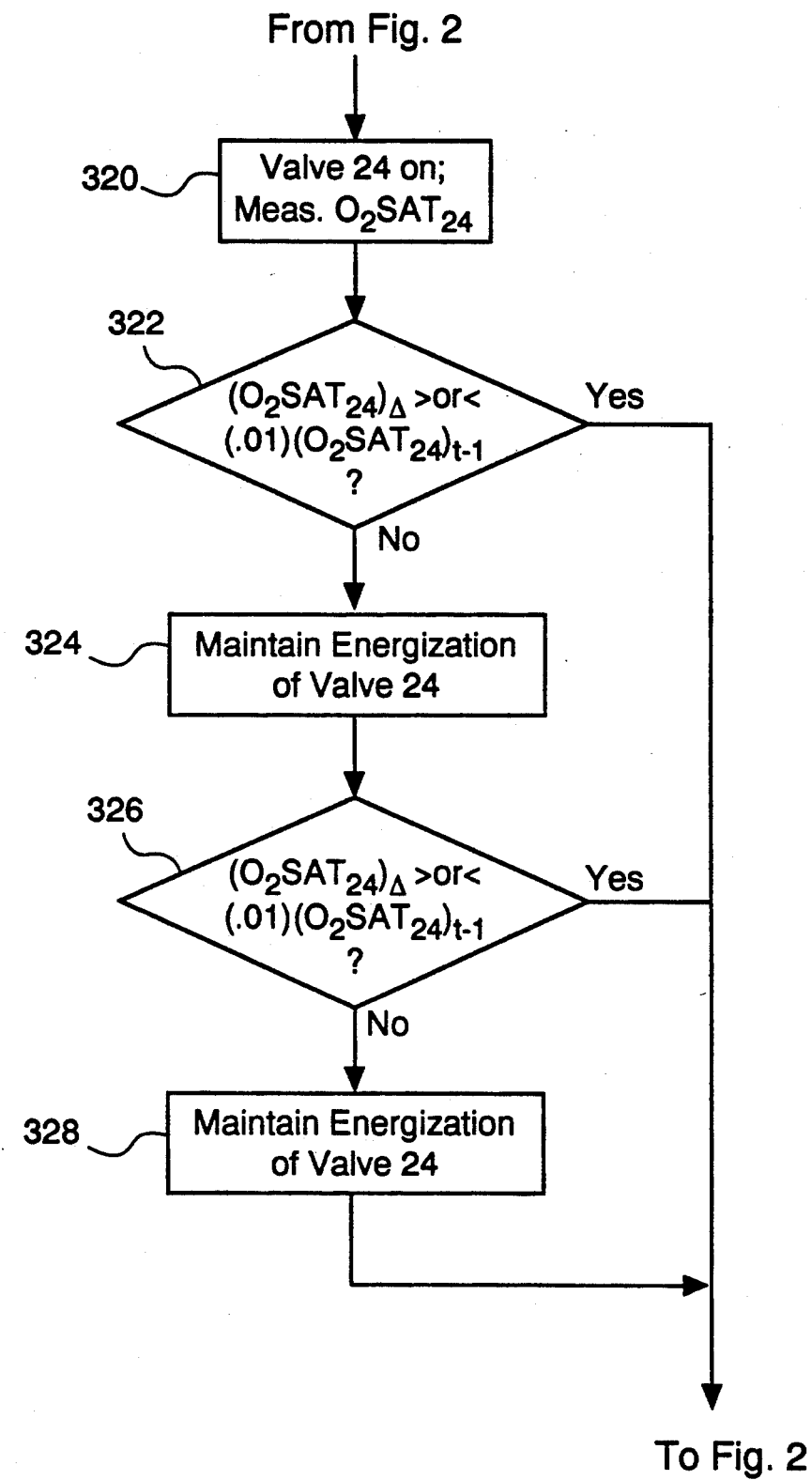
FIG. 7 is a flowchart detailing the Dominant Valve Mode oxygenation strategy utilized by the present invention when valve 24 of FIG. 2 is completely dominant.
Figure 8:
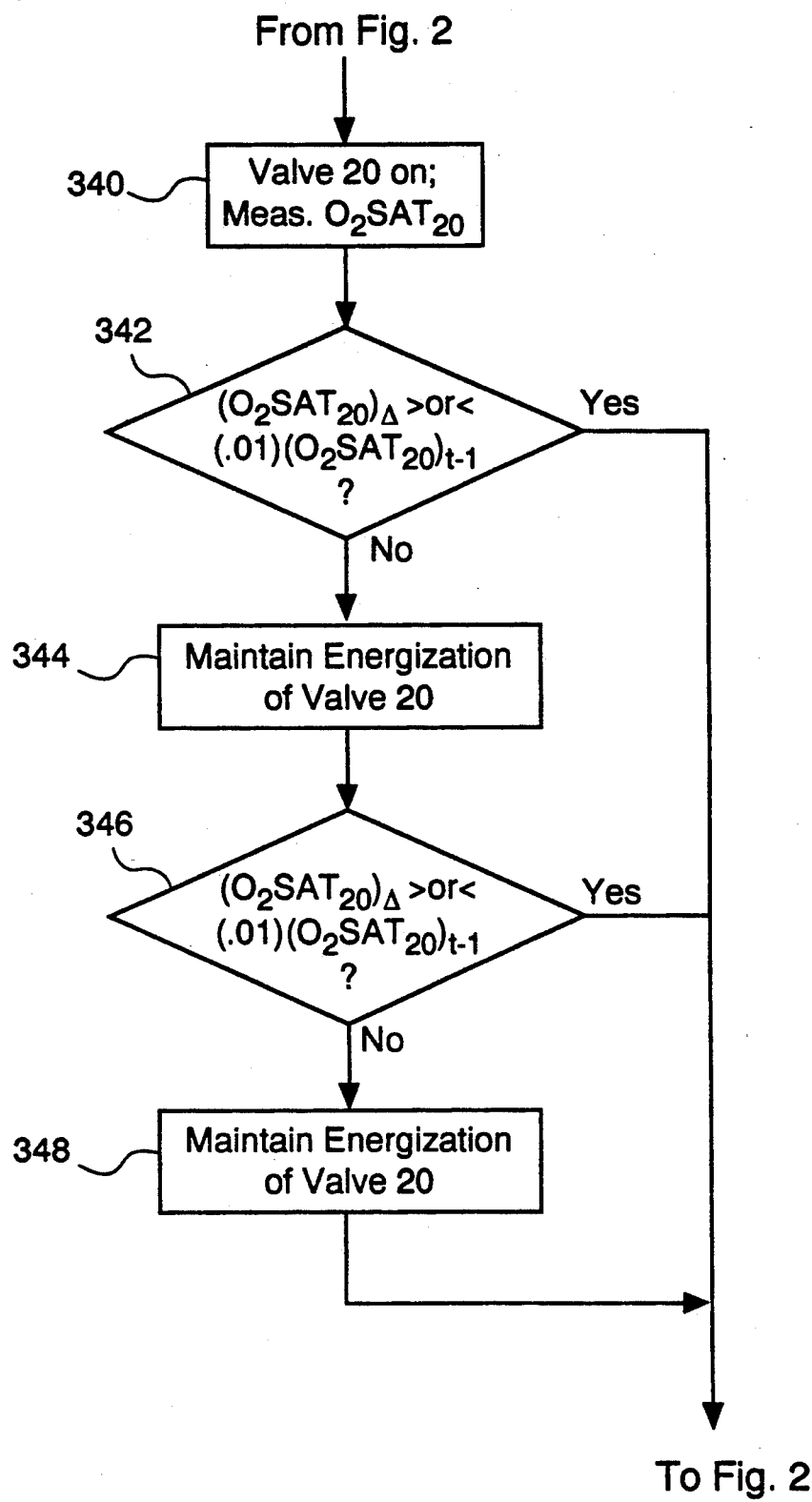
FIG. 8 is a flowchart detailing the Dominant Valve Mode oxygenation strategy utilized by the present invention when valve 20 of FIG. 2 is completely dominant.

Referring once again to FIG. 2b-2f, it can be seen that the remainder of the flowchart consists of the steps described above arranged in a generally repetitive pattern. As previously described, these steps compare pairs of valves to determine complete dominance, which is achieved when the same valve dominates the other valves for three consecutive test intervals. For example, at step 100 valve 22 is the dominant valve. If valve 22 dominates valve 24 (decided at step 106) and valve 22 dominates valve 20 (decided at step 114), then valve 22 is completely dominant and the Dominant Valve Mode of FIG. 5 is entered at step 116. A similar result for valve 22 could be achieved through the branch identified by steps 142, 158 and 166, or through the branch identified by steps 184, 192 and 166. It should be appreciated therefore, that valve 24 could be the dominant valve if it dominates for three consecutive intervals. For example, if valve 24 first dominates valve 22 (decided at step 106), then dominates valve 20 (decided at step 176) and lastly dominates valve 22 again (decided at step 184), valve 24 is completely dominant and the Dominant Valve Mode for valve 24, shown in FIG. 7, is entered at step 194. Steps 320-328 of FIG. 7 are substantially similar to steps 300-308 of FIG. 6, which were described in greater detail above. A similar result for valve 24 could be achieved through the branch identified by steps 124, 142 and 150, or by the branch identified by steps 210, 220 and 150. Similarly, it should be appreciated that valve 20 could be the dominant valve if it dominates for three consecutive intervals. For example, if valve 20 first dominates valve 22 (decided at step 114), then dominates valve 24 (decided at step 124) and lastly dominates valve 22 again (decided at step 132), valve 20 is completely dominant and the associated Dominant Valve Mode is entered at step 134. A similar result for valve 20 could be achieved through the branch identified by steps 176, 202 and 210, or through the branch identified by steps 192, 124 and 132. Steps 340-348 of FIG. 8 are substantially similar to steps 320-328 of FIG. 7 and steps 300-308 of FIG. 6, which were described in greater detail above. It should be noted that, with reference to FIG. 7, when leaving the dominant valve mode of valve 24, control flow jumps back to step 170 of FIG. 2a and that, with reference to FIG. 8, when leaving the dominant valve mode of valve 20, control flow jumps back to step 118 of FIG. 2b. Finally, the upper test condition of FIG. 3 (i.e. $TC_1$) is preferably present between every state in FIG. 4 (except step 250) and FIG. 5, and is exercised every five seconds for each state, as described above. If the condition is not satisfied, control flow jumps to the next state.

Neonatal Nasal Prong Oxydosimeter

Figure 9:
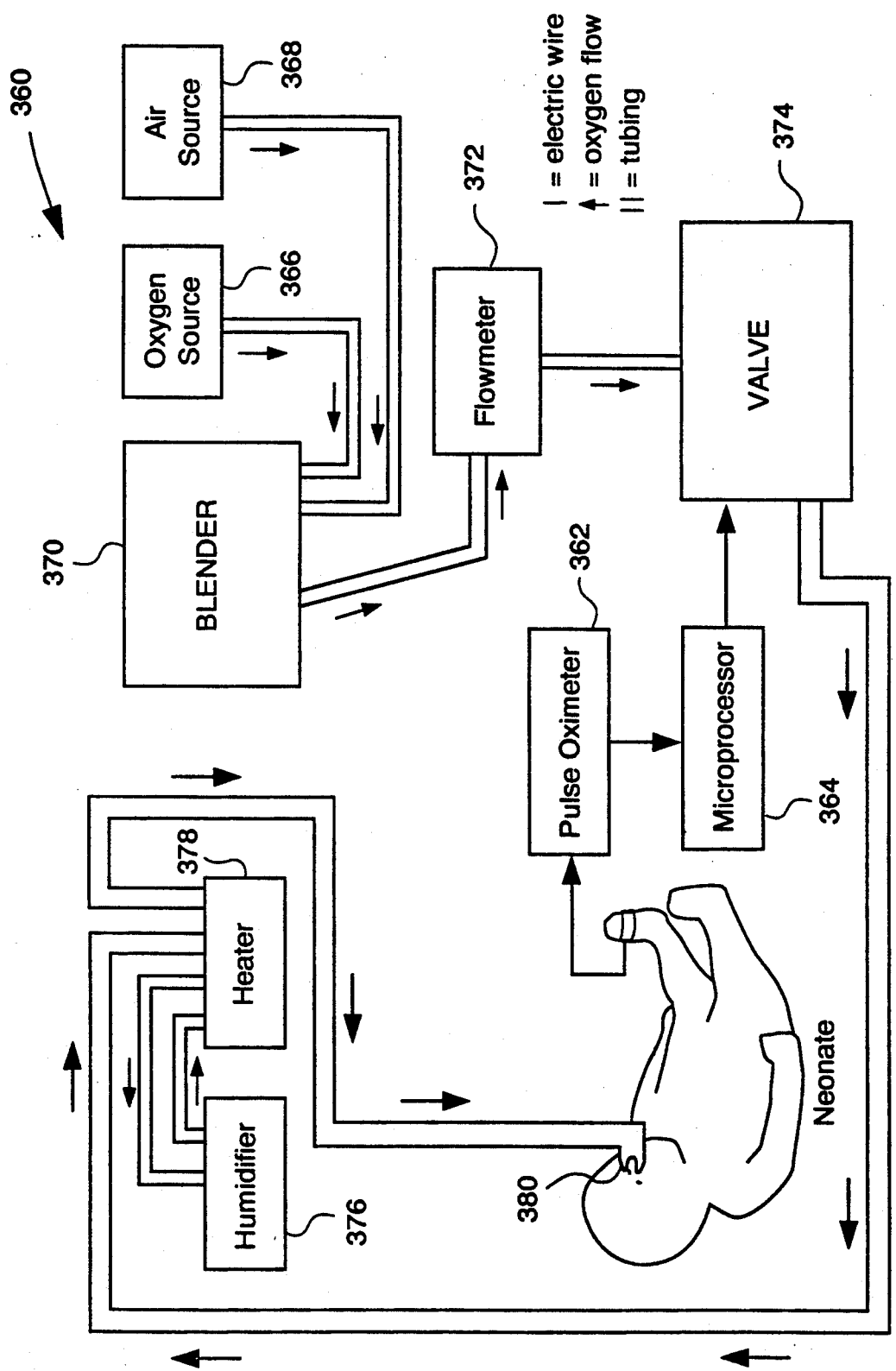
FIG. 9 is a block diagram of the second oxydosimeter embodiment of the present invention, for use as a neonatal nasal prong oxydosimeter.

Referring now to FIG. 9, there is shown the second oxydosimeter embodiment of the present invention shown generally by reference numeral 360, for use as a neonatal nasal prong oxydosimeter. As illustrated, the oxydosimeter 360 includes a pulse oximeter 362 for attachment preferably to the foot of a neonate shown generally by reference numeral 364. The pulse oximeter 362 supplies oxygen saturation data and pulse rate data to the microprocessor 364, which executes a control strategy to maintain oxygen saturation levels in the neonate within predetermined ranges, as described in greater detail below. In this embodiment, the oxygen saturation data is mean oxygen saturation.

With continuing reference to FIG. 9, the neonatal nasal prong oxydosimeter 360 also includes a pressurized oxygen source 366 and a pressurized air source 368, both of which are in fluid communication with a blender 370, such as the 3800 Microblender commercially available from Bird Products Corporation. The blender 370 preferably provides oxygen at varying concentrations to a flowmeter 372, such as Model 1333HT, commercially available from the Mada Corporation of Carlstadt, N.J., United States of America. Most preferably, the blender 370 delivers oxygen having a 100% concentration in this embodiment. The flowmeter output (e.g. set at 24 L/min) is supplied to a valve shown generally by reference numeral 374, which is controlled by the microprocessor 364 to dispense proper amounts of oxygen to the neonate. In the preferred embodiment, the flowmeter output is set to about 2 L/min. In the illustrated embodiments, the valve 374 is a thirty-eight increment, continuous electric valve, such as that disclosed in the '773 patent, capable of delivering oxygen at a rate ranging from about 1/32 L/min to about 2 L/min. As shown, oxygen from the valve 374 is delivered through tubing to a humidifier 376 and an optional heater 378, prior to being delivered to the neonate via nasal prongs 380.

Figure 10:
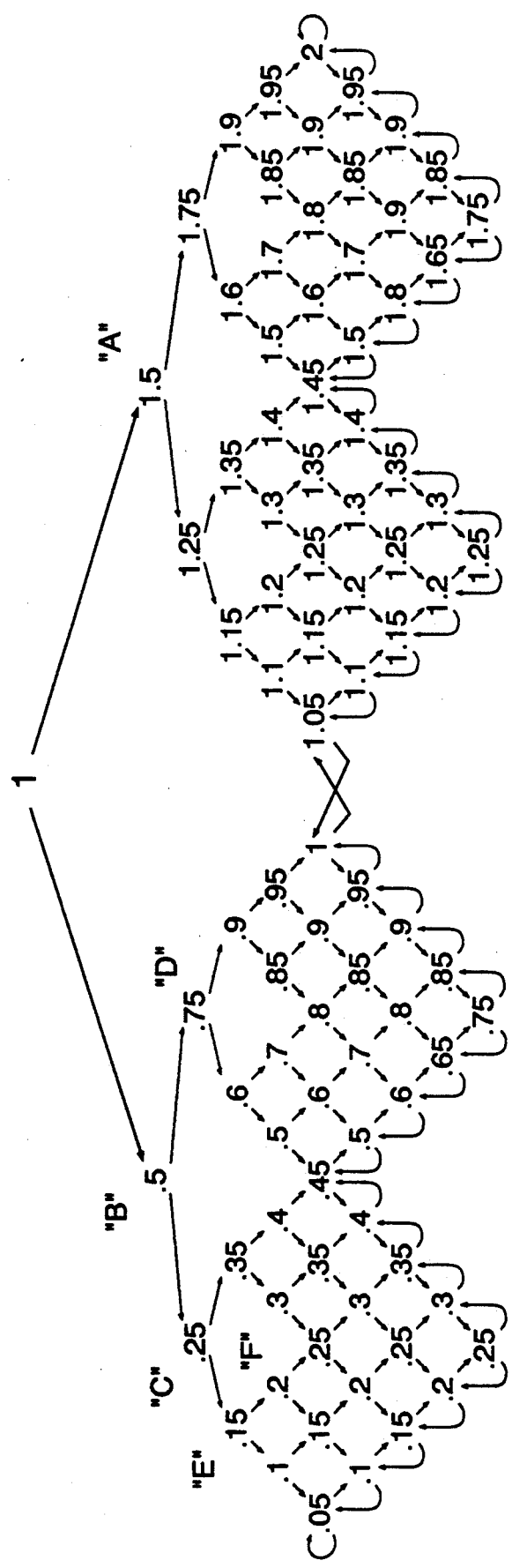
FIG. 10 is a graphical representation of an oxygenation chart of the present invention for use with the neonatal nasal prong oxydosimeter shown in FIG. 9.

Referring now to FIG. 10, there is shown a graphical representation of an oxygenation chart for use with the neonatal nasal prong oxydosimeter shown in FIG. 9. In the preferred embodiment, each number represents a oxygenation state defining the rate of oxygen delivery in liters/minute (L/min). After about five seconds at a particular state, the microprocessor measures the mean oxygen saturation (O₂SAT) of the neonate utilizing the pulse oximeter. The relative direction of movement within the chart to the next state depends on the measured oxygen saturation. For example, in the preferred embodiment, if the measured oxygen saturation is a lower value, the next state is generally toward the right side of the chart, which corresponds to higher oxygen delivery rates. If, however, the oxygen saturation is a higher value, the next state is generally toward the left side of the chart, which corresponds to lower oxygen delivery rates. If a variable solenoid valve allows 0.03 (i.e. 1/32) L/min flow rate, the portion of FIG. 10 enclosed in phantom may be slightly modified. Most preferably, the phantom box (vertices of 0.15, 0.05, 0.15 and 0.25) is replaced with a larger box having vertices of 0.15, 0.03, 0.15 and 0.27 flow rates, the flow rates varying from vertex to vertex by 0.03 L/min increments. All rules described for FIG. 10 apply to the modified chart. It should be appreciated that other flow rate increments could be specified and that other portions of FIG. 10 could be similarly modified.

With continuing reference to FIG. 10, spacing of the states as illustrated was arbitrarily prolonged for descriptive purposes. To effect a 5% increase in flow rate using a 0.05 L/min as the increment, the 0.05 L/min state is too large for flow rates less than 0.8 L/min. By using a 0.03 L/min increment, that limit drops to 0.6 L/min. If a 0.03 L/min increment is utilized, as discussed above, throughout the chart, sixty-seven (67) increments would result. The preferred embodiment of this device and all similar devices in this document will utilize 0.03 L/min increments and even smaller flow rates when they become available for states from 0.03-0.27 L/min inclusive and 0.05 L/min increments for all states ≧1 L/min. For descriptive purposes, all further discussion relating to FIG. 10, unless otherwise stated, will use 0.05 L/min increments.

Figure 11:
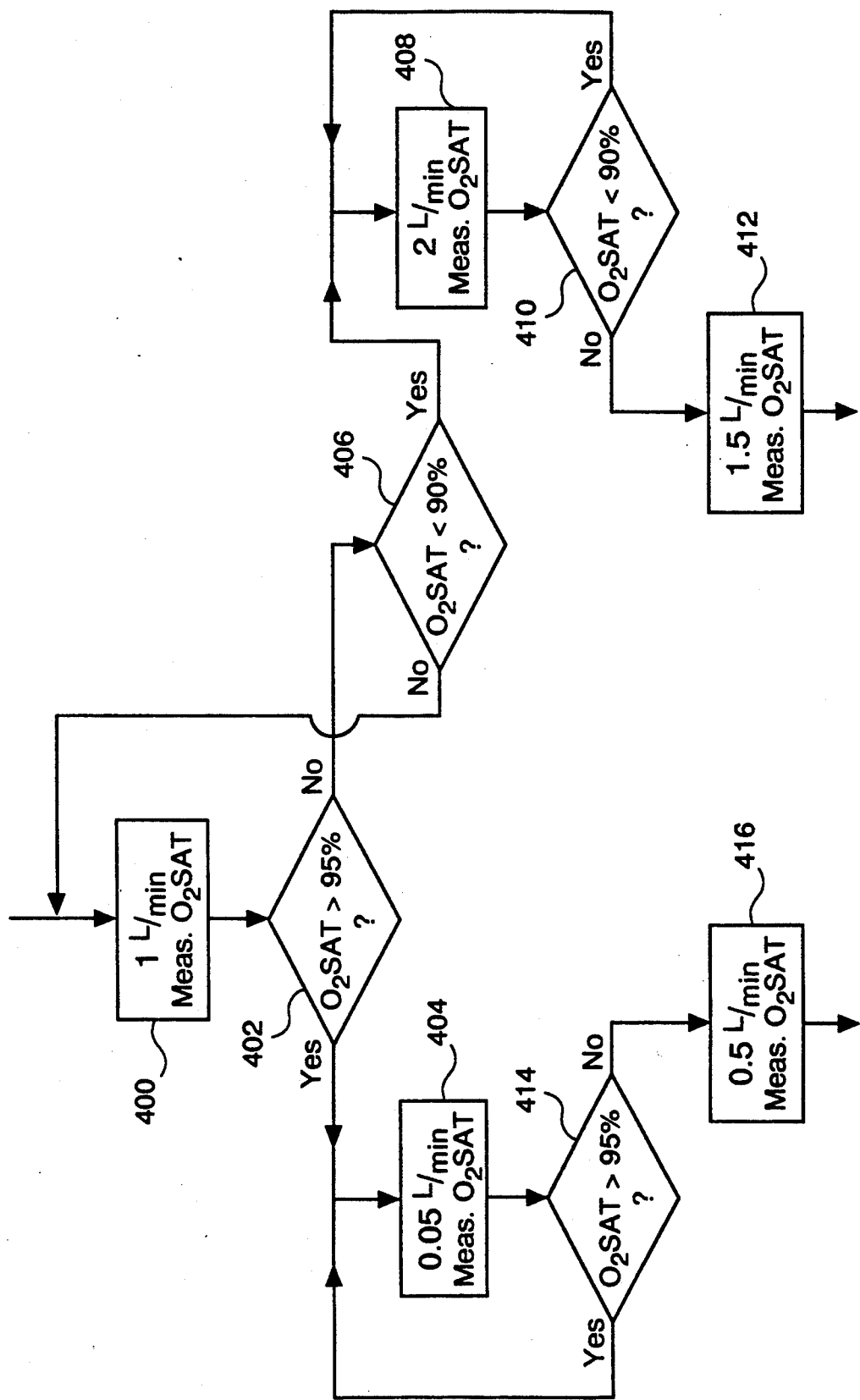
FIGS. 11 and 12 are flowcharts detailing the oxygenation strategy of the present invention for use with the oxygenation chart of FIG. 10 with the neonatal nasal prong oxydosimeter.

Referring now to FIG. 11, there is shown a flowchart detailing the control strategy of the present invention for use with the neonatal nasal prong oxydosimeter while operating in a normal oxygen state. Low oxygen states are all states with flow rates of 0.05– 0.45 L/min inclusive. In the series shown in FIG. 13, the 0.6 L/min value does not signify the value of the present state. It is the largest value or upper limit of a group of maximum oxygen states for the above range. Maximum oxygen states are a number of states, which, after following the appropriate condition (i.e. if the oxygen saturation is less than X), increase oxgenation in a step-like fashion. The value of a particular maximum oxygen state is given by mode MX, as described in greater detail below. FIG. 13 shows five such states, connected in series. The condition in mode MX occurs below every other condition shown. Mode X describes a network. The total number of states that can be activated by the microprocessor is 24.

Control then passes to the chart's apical 0.5 L/min state's maximal oxygen state value, which is closest to the last state on the high side (if the value of the maximum oxygen state is greater than half the difference between the largest and the smallest values of the maximum oxygen state in the last network). The mirror image holds true when considering minimal oxygen states (i.e. use less rather than greater). If not, control follows the arrows in the chart to the right at the same or next highest maximal energy state as the last network's. The above discussion also applies to mode Y MY throughout, except there are no limits on the smallest value of the minimum oxygen state, except 0.05 L/min. After 24 minimal oxygen states have passed, the ECU passes control to the 0.05 L/min state. The other three ranges are 0.5–1 L/min, 1.05–1.45 L/min and 1.5–2 L/min, respectively; the maximum oxygen state's largest value in the first range is the apical 1 L/min, chosen so the entire apical chart placement mechanism may be repeated to prevent large jumps in flow rate to neonates usually requiring low flow rates. At the bottom of this series, to the right, mode X is not used, and mode Y is not used to the left. An alarm will sound whenever this step is activated, allowing therapists to switch to another oxygen modality if they feel the flow rate is excessive.

The other two limits are the apical 1.6 and the apical 2 L/min states, respectively. For three of these ranges, the next state directing to mode X at a maximum oxygen state value closest to the last state and on the high side and entered whenever 24 steps of a network of maximum oxygen states have been completed is the apical 1 L/min, the apical 1.5 L/min, and the 2 L/min states, respectively. For the given ranges, the next state directing to mode Y at a minimum oxygen state value closest to the last state on the low side and entered when 24 steps of a network of minimum oxygen states have been completed is the apical 0.4 L/min, the apical 0.95 L/min and the apical 1.4 L/min, respectively.

Even though the fully automated respirator and the neonatal oxydosimeter will be presented later, it is best to give their ranges here, where they may be incorporated by reference. The ranges as used in the above analysis are: 23.5% oxygen concentration—35.5%; 39%–50%, 52.5%–75%, and 80%—100%, respectively. The next state directing to mode X at a maximum oxygen state value closest to the last state on the high side and entered whenever 24 steps of the last maximum oxygen state have been completed is the apical 39% oxygen concentration, 52.5%, the apical 80% and 100% oxygen concentrations, respectively. There are no largest or smallest values of the maximum or minimum oxygen states other than 100% and 23.5% oxygen concentration, respectively. The next state directing to mode Y at a minimal oxygen state value closest to the last state and on the low side, whenever 24 steps of a network of minimum oxygen states have been completed is 23.5%, the apical 36.5%, the subapical 50% and the apical 75%, respectively. The purpose of the above jumps is to quickly oxygenate and deoxygenate when speed is of great importance.

If maximal or minimal oxygen states are terminated before 120 seconds, control passes to the next state on the right or the left, respectively, as seen on the chart.

For purposes of this discussion, mode X is best described as follows. Step 1: take 5% of the value of the last state that produced the first oxygen saturation below the lower normal limit of the prescribed range. Step 2: add it to the last state. This is the $n^{th}$ maximum oxygen state. Step 3: measure mean oxygen saturation every 10 seconds. Step 4: let 10 seconds pass. Step 5: apply this condition—which is below all other conditions in this path: if the oxygen saturation is less than 5% of the difference between the last state of step 1 and the low normal limit of the prescribed range of oxygen saturation. Step 6: if the answer to the condition is yes, double the percentages in steps 1 and 5 and go to step 1. Continue until either of the above conditions directs to step 7 or higher conditions direct elsewhere, or step 8 or 9 is reached. Step 7: if the condition in step 4 yields a no answer, go to step 1, using the same percentages in steps 1 and 5 as are presently listed. Continue until either the condition in step 5 directs to step 6, or step 9 is reached or higher conditions direct elsewhere. Step 8: after 30 seconds, step 6 directs to the state 3 positions up the series from its present position. Step 9: after about 120 seconds, control passes to the "next state directing to mode X," described above in relation to the discussion of low oxygen states for the neonatal nasal prong oxydosimeter. All above calculations are rounded off to the next highest state even if the calculated value is less than half their difference. An alarm will preferably sound after about 10 seconds.

For purposes of this discussion, mode Y is described as follows. Step 1: take 5% of the value of the last state that produced the first oxygen saturation above the upper limit of the prescribed range. Step 2: subtract it from the last state. This is the $n^{th}$ minimum oxygen state. Step 3: measure mean oxygen saturation about every 10 seconds. Step 4: let 10 seconds pass. Step 5: present this condition—which is below all other conditions in the path: if the oxygen saturation is greater than 5% of the difference between the last state of step 1 and the high normal limit of the prescribed range of oxygen saturation. Step 6: if the answer to the condition is yes, double the percentages in steps 1 and 5 and go to step 1. Continue until either the condition directs to step 7, or step 8 or 9 below is reached, or higher conditions direct elsewhere. Step 7: if the condition in step 4 yields a negative answer, go to step 1 using the same percentages used in steps 1 and 5. Continue until either the condition of step 5 directs to step 6, or other conditions direct otherwise, or step 9 is reached. Step 8: after 30 seconds, step 6 directs to the state 3 position of the series from its present position. Step 9: after 120 seconds, control passes to the next state described above in relation to the discussion of low oxygen states for the neonatal nasal prong oxydosimeter. All above calculations are rounded off to the next lowest state even if the calculated value is greater than half their difference. An alarm will sound after 10 seconds.

Until stated otherwise, all of the following examples will be described for maximal or minimal states terminated in greater than 120 seconds but with a state value less than 50% of the largest maximum oxygen state or greater than 50% of the difference between the smallest and largest minimal oxygen state.

With combined reference to FIGS. 10 and 11, at step 400 the microprocessor initially controls the valve to deliver oxygen at a rate of 1 L/min and after thirty seconds measures the oxygen saturation associated with that flow rate. Just prior to step 400 and not shown are eleven five second 1 L/min states identical to step 400 and eleven decision boxes identical to step 402 with the "no" side of the condition box connected serially, ending at step 400, and the "yes" side connected to step 416. These additional steps are connected in series with step 400. The microprocessor determines whether the oxygen saturation of the patient is greater than 95%. If it is, the microprocessor adjusts the oxygen dosage to 0.5 L/min. If not, dosage remains at 1 L/min. All listed states for this device last five seconds.

As shown in FIG. 11, at step 402 the microprocessor determines whether the oxygen saturation ($O_2SAT_{1L}$) of the patient is greater than 95%. If it is, a minimal $O_2$ state is reached, as described in greater detail above. For every minimal oxygen state, there are a number of previous steps, analogous to FIG. 13b, connected in series and parallel as described. Control follows Mode Y.

Also, a condition identical to step 414 follows each step. If the answer to the condition is "yes", control passes down the sequence. If "no", control passes to step 416, as previously described. It should be noted that two conditions are working above. One occurs every five seconds, the other every ten seconds, as previously described.

With continuing reference to FIG. 11, if $O_2SAT_{1L}$ is less than 95%, at step 406 the microprocessor determines whether $O_2SAT_{1L}$ is less than 90%. If the oxygen saturation is not less than 90% at step 406, (i.e. between 90% and 95%), control flow returns to the previously mentioned sequence leading to step 400 wherein 1 L/min of oxygen is delivered. If the oxygen saturation is less than 90%, a maximal $O_2$ state is reached. For every maximal oxygen state, there are a number of previous steps, analogous to FIG. 13b, connected in series and parallel. Control follows Mode X, described above.

Also, a condition identical to step 410 follows each step. If the answer to the condition is "yes", control passes down the sequence. If "no", control passes to step 412. The previous rules above step 412's particular maximum oxygen state should be kept in mind. It should be noted that two conditions are working above. One occurs every five seconds, the other every ten seconds (i.e. Mode X's condition).

With continuing reference to FIG. 11, at step 410 the microprocessor determines whether $O_2SAT_{2L}$ is less than 90% and, if it is, control flow returns to step 408 wherein 2 L/min of oxygen signifies a maximum value of a maximum $O_2$ state, which continues until the oxygen saturation exceeds 90%. If $O_2SAT_{2L}$ is greater than 90% percent, the next state is established, wherein 1.5 L/min of oxygen signifies the location on the chart of a maximum $O_2$ state applied to the neonate at step 412. This state is indicated at point "A" in FIG. 10.

As shown in FIG. 11, after measuring the oxygen saturation associated with a 0.05 L/min flow rate at step 404, the microprocessor again determines whether the oxygen saturation still exceeds 95% at step 414. If the oxygen saturation continues to be greater than 95%, control flow jumps back to the maximal oxygen state as described above. This process continues until the oxygen saturation drops below the 95% level, at which point the microprocessor controls the valve to deliver oxygen at 0.5 L/min's minimum oxygen state at step 416 and measures the associated oxygen saturation ($O_2SAT_{.5L}$) after five seconds. This corresponds to state 0.5 indicated at point "B" on FIG. 10.

Figure 12:
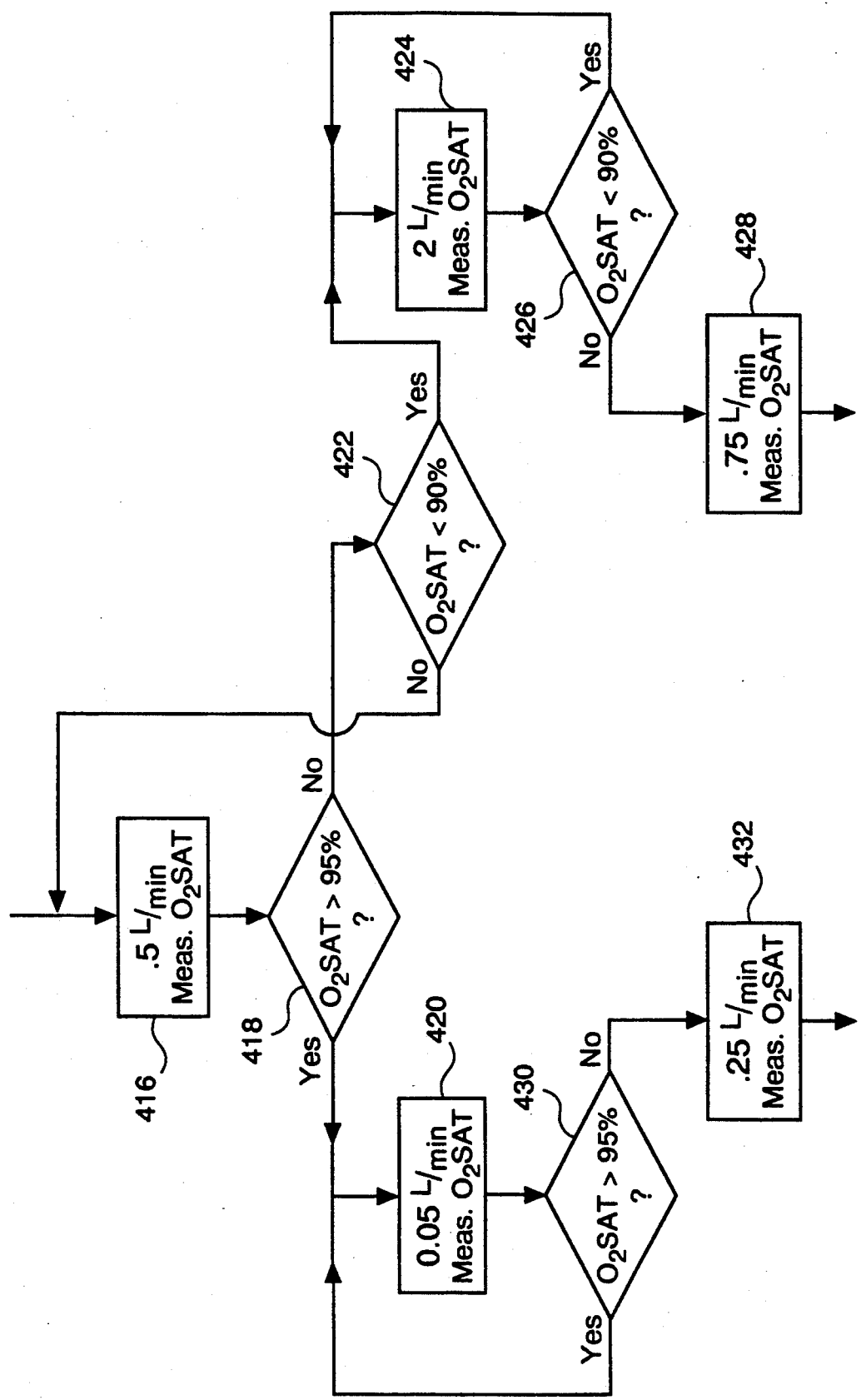

To continue the strategy from step 416 and move along the chart of FIG. 10 from state 0.5 to the next state, the flowchart of FIG. 11 is generally repeated, as shown in FIG. 12. Thus, steps 416–432 are executed in the manner that steps 400–416 of FIG. 11 were executed, to determine whether the next minimal or maximal oxygen state, respectively, stems from 0.25 (point "C" on FIG. 10) or 0.75 (point "D" on FIG. 10). That is, after oxygen has been flowing at 0.5 L/min for five seconds, the microprocessor determines whether $O_2SAT_{.5L}$ is greater than 95% at step 418. If it is, the microprocessor adjusts the oxygen dosage, reducing it to the minimal oxygenation state leading to 0.05 L/min, the lowest delivery rate, at step 420. If the oxygen saturation is less than 95%, at step 422 the microprocessor determines whether the oxygen saturation is less than 90%. If the oxygen saturation is less than 90%, the microprocessor controls the valve to deliver an oxygen dosage to the maximal oxygen state signified by 2 L/min at step 424 for about five seconds, after which the microprocessor measures the new oxygen saturation ($O_2SAT_{2L}$). If the oxygen saturation is not less than 90% at step 422, (i.e. between 90% and 95%), control flow returns to step 416 wherein 0.5 L/min of oxygen is delivered. At step 426, the microprocessor determines whether $O_2SAT_{2L}$ is less than 90% and, if it is, control flow returns to step 424 wherein 2 L/min represents the maximal oxygen state delivered until the oxygen saturation exceeds 90%. If $O_2SAT_{2L}$ is greater than 90% percent, the next state is established and 0.75 L/min's maximal oxygen state is delivered to the neonate at step 428.

As shown in FIG. 12, after measuring the oxygen saturation associated with a 0.05 L/min's minimal oxygen state's flow rate at step 420, the microprocessor again determines whether the oxygen saturation still exceeds 95% at step 430. If the oxygen saturation continues to be greater than 95%, control flow jumps back to step 420 such that a minimal oxygen state represented by 0.05 L/min continues to be delivered to the neonate. This process continues until the oxygen saturation drops below the 95% level, at which point a new state is established and the microprocessor controls the valve to deliver oxygen at a rate of 0.25 L/min at step 432 and measures the associated oxygen saturation after five seconds. From this point on, when a state in the text or figures represents a minimal or maximal energy state and is written as a representation of that fact further clarification will not ensue. This applies to all three devices to be described.

Figure 13A:
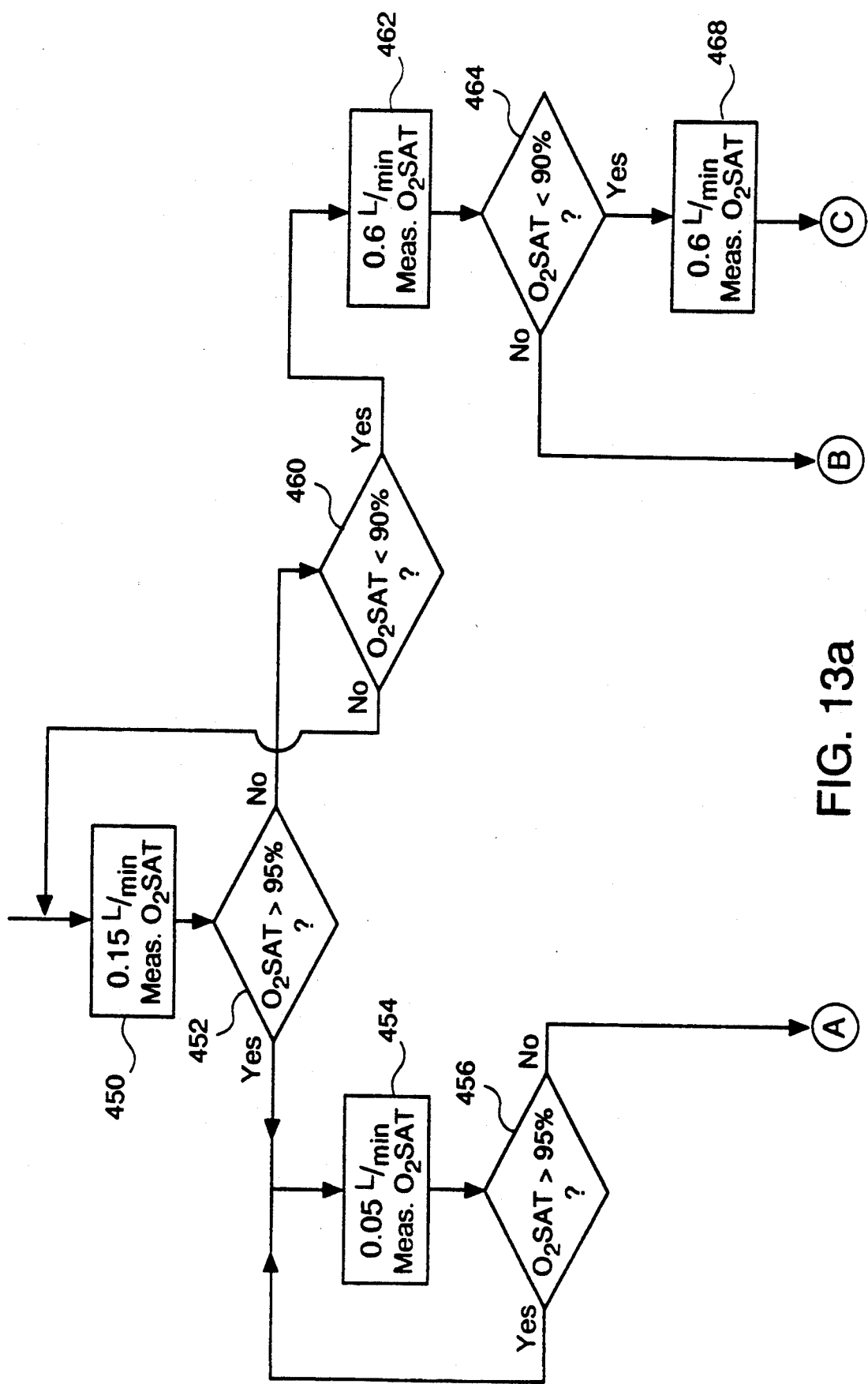
FIGS. 13a–13b are a flowchart detailing the oxygenation strategy for the neonatal nasal prong oxydosimeter operating in a low oxygen state.
Figure 13B:
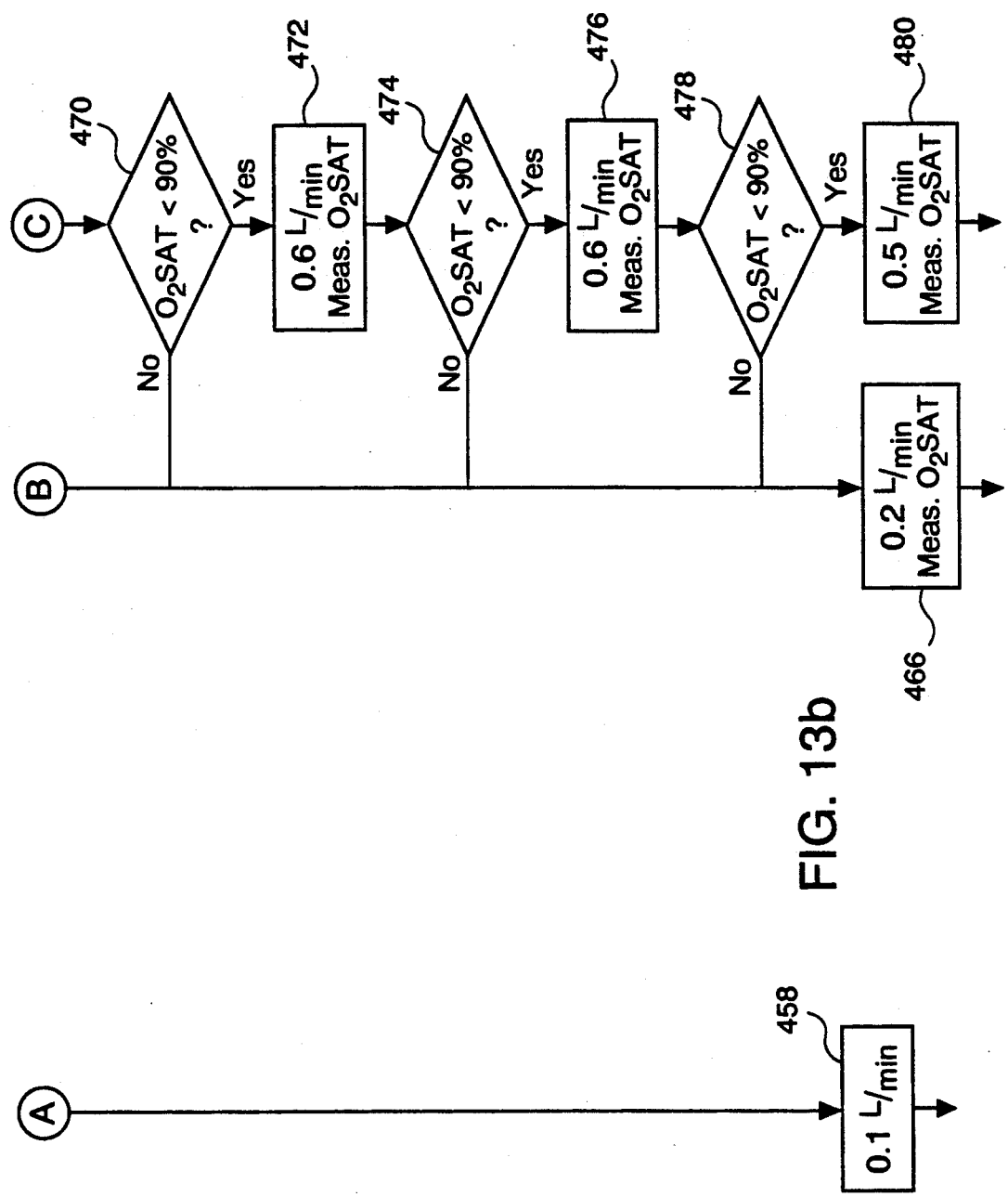

With reference now to FIGS. 13a-13b, there is shown a flowchart for the oxygenation strategy utilized by the neonatal nasal prong oxydosimeter during a low oxygen state. As previously described, if conditions lead a state to travel to the right in FIG. 10 and if the resulting states oxygen saturation multiplied by three is less than 2 L/min, the oxydosimeter preferably operates in a low oxygen state. The low oxygen state will be described with reference to FIG. 10, beginning at the 0.15 state indicated by point "E". The 0.15 state is a low oxygen state, since 3(0.2) <2. As best shown in FIG. 13a, at step 450, the microprocessor controls the valve to deliver a dosage of 0.15 L/min of oxygen to the neonate. After about five seconds, the oxygen saturation is measured. At step 452, the microprocessor determines whether the oxygen saturation is greater than 95%. If it is, a minimal oxygen state oxygen dosage is administered to the neonate just prior to step 454. After about five seconds at the minimal oxygen dosage, the microprocessor again determines the oxygen saturation ($O_2SAT_{.05L}$). If the oxygen saturation of the patient 14 is greater than 95% at step 456, control sequences to step 454 and oxygen delivery continues at the minimal oxygen dosage. If the oxygen saturation is less than 95%, the microprocessor controls the valve to deliver 0.1 L/min of oxygen to the neonate at step 458 of FIG. 13b.

With continuing reference to FIGS. 13a-13b, if the oxygen saturation was less than 95% at step 452, control flow skips to step 460, wherein the microprocessor determines if the oxygen saturation is less than 90%. If it is not, (i.e. if the oxygen saturation is between 90% and 95%), control flow returns to step 450, and the oxygen delivery continues at 0.15 L/min. If the oxygen saturation is less than 90% at step 460, it is desirable to increase the oxygen saturation, so the next state is established. In the preferred embodiment, the next state is the 0.2 state indicated by point "F" on FIG. 10. Most preferably, at step 462 the microprocessor controls the valve to deliver 0.6 L/min i.e. three times 0.2 L/min) of oxygen. In FIGS. 13a-13b, steps 462, 468, 472 and 476 contain a value 0.6 L/min—this is not the value of the state, but rather the value of the maximal low oxygen state. Also, only four sates are pictured. In fact, there are nine low oxygen states which may also be considered high oxygen states. The first three steps increase the oxygen concentration by 5% of the last step. The next two step by 10%. The next two steps by 20% increments, and the next step by a 30% increment. Thereafter, 0.6 L/min is given. The purpose of this only embodiment of a low oxygen state is to help neonates with larger flow rates, who mistakenly arrived in a low energy state, get out without being trapped at step 476 on a fraction of the oxygen that is needed.

With continuing reference to FIG. 13a, after about five seconds, the microprocessor measure the associated oxygen saturation ($O_2SAT_{.6L}$). At step 464, the microprocessor determines whether $O_2SAT_{.6L}$ is less than 90%. If it is not less than 90%, control flow jumps to step 466 at which point a reduced oxygen delivery rate (e.g. 0.2 L/min) is established. If $O_2SAT_{.6L}$ is less than 90%, the microprocessor continues to deliver oxygen at the maximal oxygen state. Thereafter, at steps 470–478, the microprocessor continues to test for time at which the oxygen saturation exceeds 90%, and continues to administer oxygen at 0.6 L/min until 90% is achieved. If a below 90% condition persists for more than twelve intervals, at step 480 the oxydosimeter operates in the 0.5 state indicated by point "B" in FIG. 10. It should be appreciated that the 0.5 state represents a position in the chart which allows the oxydosimeter to move to other states representing larger amounts of administered oxygen faster. For example, from the 0.5 state, the oxydosimeter can move to the 0.75 state (point "D") and then onto the 0.9 state. (QUERY: What's the difference? From the 0.2 state, the 0.25 state is next and 3(0.25)=0.75 L/min, the same as if you moved from 0.5 to 0.75 directly. Similarly, from 0.25 go to 0.3 and 3(0.3)=0.9 L/min.)

In another embodiment of the present invention, the neonatal nasal prong oxydosimeter has a plurality of operating modes based on varying trigger oxygen saturation levels. For example, instead of maintaining oxygen saturation between 90% and 95% as previously described, the oxydosimeter can function to maintain oxygen saturation between 88% and 92%, between 95% and 99%, or between 92% and 97%. These changes are easily made and, except for these changes, the control strategy remains the same. It should be appreciated that this feature allow therapists and physicians to change the oxygen saturation ranges without having to make changes to the system hardware and without changing the entire program.

Neonatal Oxyhood Oxydosimeter

Figure 14:
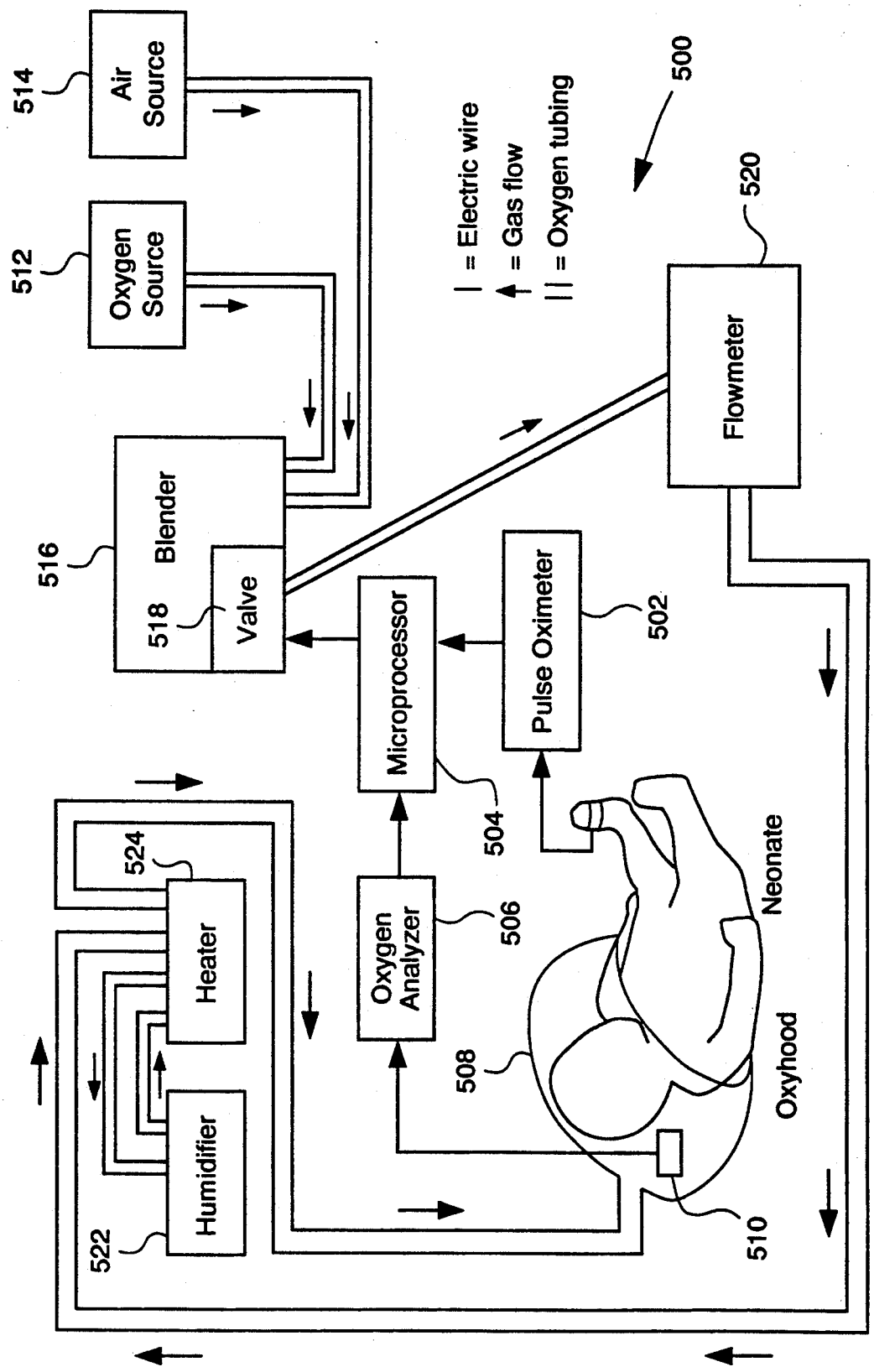
FIG. 14 is a block diagram of the third oxydosimeter embodiment of the present invention, for use as a neonatal oxyhood oxydosimeter.

Referring now to FIG. 14, there is shown the second oxydosimeter embodiment of the present invention shown generally by reference numeral 500, for use as a neonatal oxyhood oxydosimeter. As illustrated, the oxydosimeter 500 includes a pulse oximeter 502 for attachment, preferably to the foot, of the neonate. The pulse oximeter 502 supplies oxygen saturation data and pulse rate data to a microprocessor 504. For this embodiment, all oxygen saturations are mean oxygen saturations. The microprocessor also receives data from an oxygen analyzer 506. The analyzer 506 receives data relating to the oxygen concentration within the oxyhood 508 from a probe 510 positioned within the oxyhood 510, which preferably encloses the head of the neonate. The microprocessor executes a control strategy to maintain oxygen saturation levels within predetermined ranges in the neonate, based on the data from the pulse oximeter 502 and the oxygen analyzer 506, as described in greater detail below.

With continuing reference to FIG. 14, the neonatal oxyhood oxydosimeter 500 also includes a pressurized oxygen source 512 and a pressurized air source 514, both of which are in fluid communication with a blender 516, such as the 3800 blender described above. The blender 516 preferably includes a valve shown generally by reference numeral 518, which is controlled by the microprocessor 504 to dispense proper amounts of oxygen to the neonate. Most preferably, the blender 516 delivers oxygen having a variable concentration in this embodiment. In the preferred embodiment, the valve 518 is a twenty-nine increment, continuous electric valve, such as that disclosed in the '773 patent referenced above, capable of delivering oxygen at a rate ranging from about 1/20 L/min to about 2 L/min. As shown, the valve is in fluid communication with a flowmeter 520, such as the Model 1333HT flowmeter described above. The flowmeter preferably delivers about 9 L/min of oxygen through tubing to a humidifier 522 and from there, to a an optional heater 524, prior to being delivered to the neonate.

Figure 15:
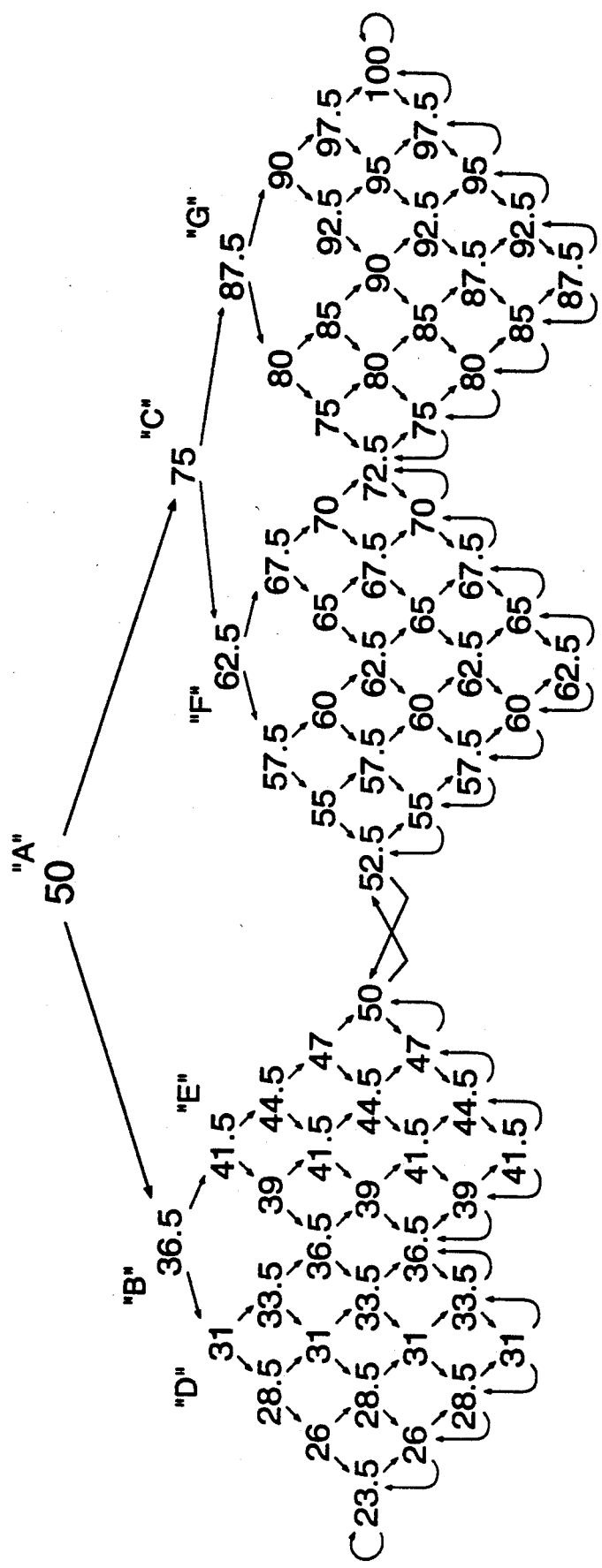
FIG. 15 is a graphical representation of an oxygenation chart of the present invention for use with the neonatal oxyhood oxydosimeter shown in FIG. 14, illustrating the oxygen concentration patterns utilized.

Referring now to FIG. 15, there is shown a graphical representation of an oxygenation chart, similar to the chart shown in FIG. 10, for use with the neonatal oxyhood oxydosimeter shown in FIG. 14. In the preferred embodiment, each number represents a state defining the oxygen concentration in percent (%). Oxygen concentration in the oxyhood, preferably maintained between about 22% and 60%, is preferably measured by the microprocessor 504 in five second intervals. The 2.5% increment is the preferred embodiment for this device and all similar devices.

Figure 16A:
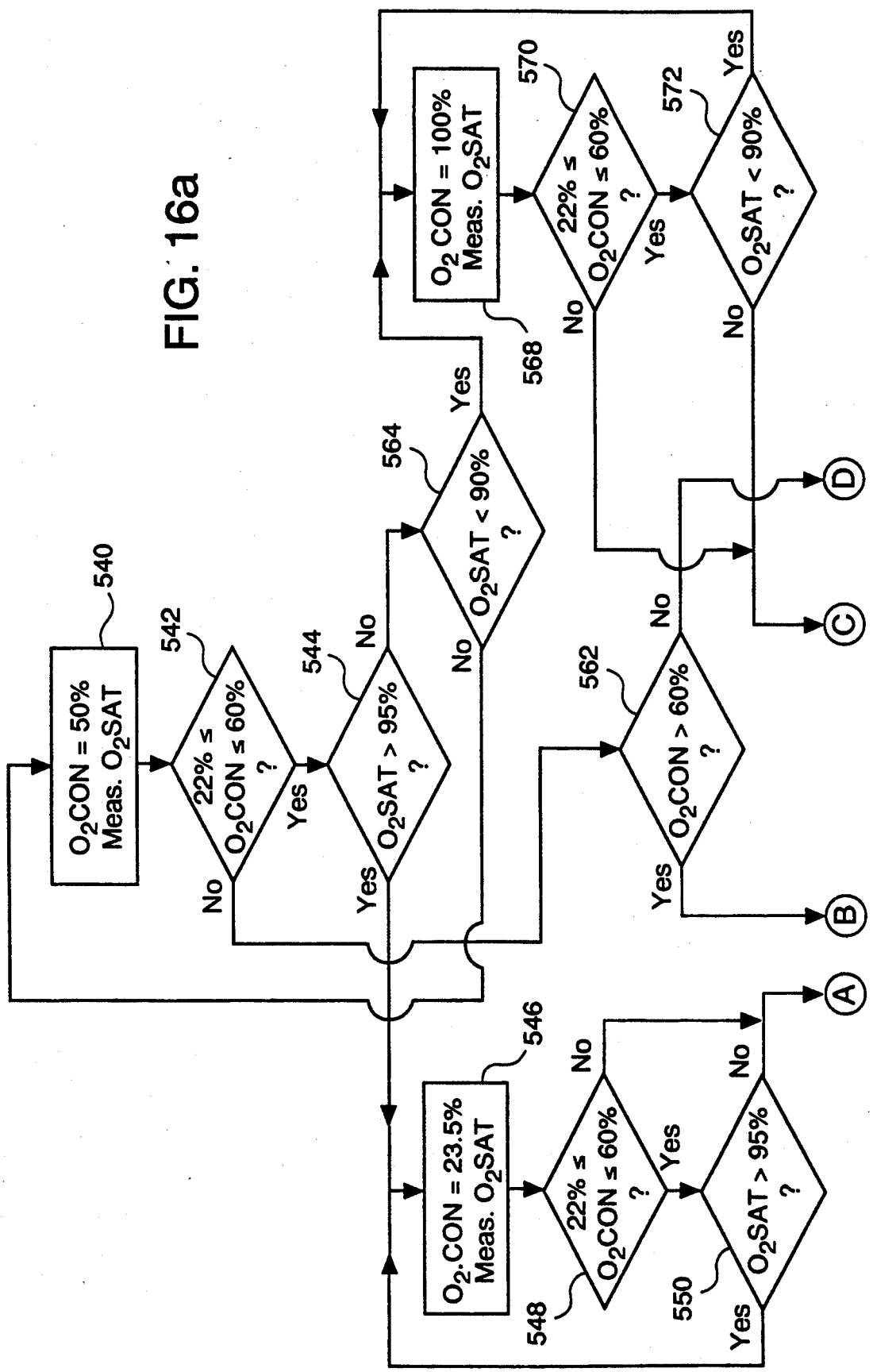
FIGS. 16a–16b are a flowchart illustrating the oxygenation strategy of the present invention for the neonatal oxyhood oxydosimeter.
Figure 16B:
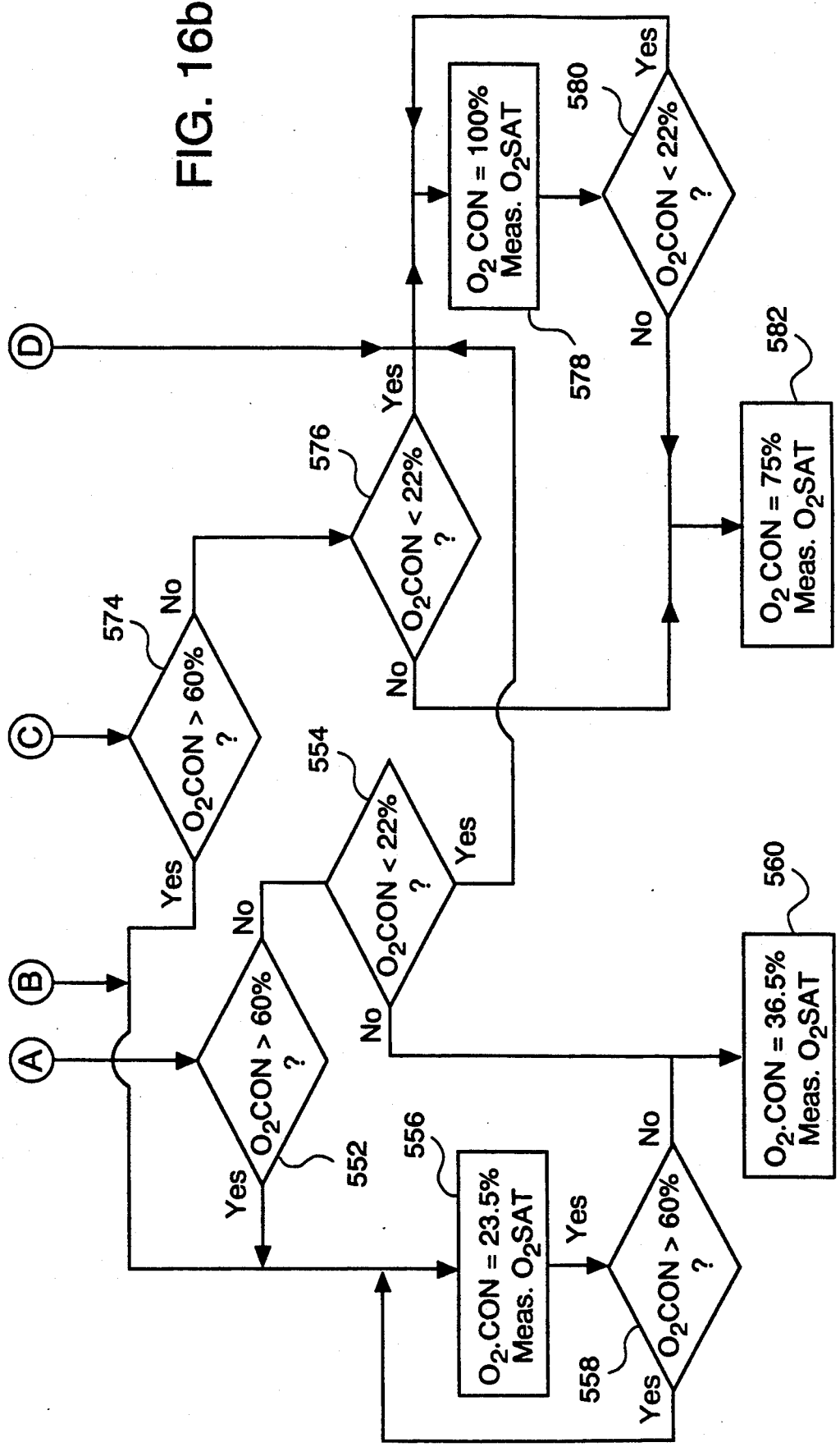

Referring now to FIGS. 16a–16b, there is shown a flowchart illustrating the oxygenation strategy of the present invention for the neonatal oxyhood oxydosimeter. The oxygenation strategy of FIGS. 16a–16b illustrates the conditions that must be satisfied prior to the movement within the chart of FIG. 15 from state to state. As best shown in FIG. 16a, at step 540 the microprocessor controls the valve to deliver oxygen to obtain a 50% concentration of oxygen at the valves, which corresponds to state "A" in FIG. 15. For ease of illustration and the sake of clarity, eleven steps identical to step 540 precede step 540 and are connected in series. A condition is present between each state to test whether the oxygen saturation exceeds 95%. If it does, control jumps to step 560. If not, continue the cascade until step 542 is reached. After about five seconds, at step 542 the microprocessor determines whether the oxygen concentration at the analyzer is between 22% and 60%, inclusive. If it is, at step 544 the microprocessor determines whether the neonate's oxygen saturation (O$_2$SAT) is greater than 95%. If (O$_2$SAT) is greater than 95%, at step 546 the microprocessor controls the valve to deliver oxygen to obtain a 23.5% concentration of oxygen in the oxyhood. After about five seconds, at step 548 the microprocessor determines whether the oxygen concentration at the analyzer is between 22% and 60%, inclusive. If it is, step 550 determines whether O$_2$SAT is <95%. If not, the microprocessor determines whether the oxygen concentration in the oxyhood is greater than 60% at step 552. If O$_2$CON is not greater than 60%, the microprocessor determines whether the oxygen concentration is less than 22% at step 554 and, if it is not (i.e. O$_2$CON is between 22% and 60%, as desired), the microprocessor controls the valve to obtain a 36.5% concentration (see state "B" in FIG. 15) at step 560. If, however, the oxygen concentration was greater than 60% at step 552, a 23.5% oxygen concentration is established at step 556 and maintained, with step 558, until oxygen concentration drops below 60%, at which point a 36.5% oxygen concentration (see state "B" in FIG. 15) is established, at step 560. Preferably, an alarm will sound if step 556 is continuously activated for greater than 10 seconds.

With continuing reference to FIGS. 15 and 16a, if the oxygen concentration was not between 22% and 60% at step 542, the microprocessor determines whether the oxygen concentration exceeds 60% at step 562. If it does, control flow skips to step 556, described above. If it does not, control flow skips to step 578, described below. If the oxygen saturation was not greater than 95% at step 544, control flow skips to step 564, wherein the microprocessor determines whether O$_2$SAT is below 90%. If it is not, control flow returns to step 540. If O$_2$SAT is greater than 90%, at step 564 the microprocessor controls the valve to obtain the maximal oxygen state at the solenoid valves. For every maximal oxygen state (i.e. 100% oxygen concentration) there are a number of previous steps, analogous to FIG. 13b, connected in series and parallel. Go to Mode X, described in greater detail above. Also, two conditions identical to steps 570 and 572 follow each step. If the answers to both conditions are "no", control passes to step 574. These conditions are on top of the condition described in Mode X. If the answers to the two conditions are "yes", control directs down the sequence. At step 570 the microprocessor determines whether the oxygen concentration at the analyzer is between 22% and 60%, inclusive. If it is, an oxygen concentration of 100% is preferably maintained by steps 568-572 until the oxygen saturation exceeds 90%, at which time the microprocessor determines whether the oxygen concentration in the oxyhood is greater than 60% at step 574, as best shown in FIG. 16b. If O$_2$CON is not greater than 60%, the microprocessor determines whether the oxygen concentration is less than 22% at step 576 and, if it is not (i.e. O$_2$CON is between 22% and 60%, as desired), control flow skips to step 582, and a 75% oxygen concentration (see state "C" in FIG. 15) is maintained in the oxyhood. If, however, the oxygen concentration was greater than 60% at step 574, control flow skips to step 556, wherein a 23.5% oxygen concentration is established and maintained with step 558 as described above. If O$_2$CON was less than 22% at step 576, a 100% oxygen concentration is preferably once again established at step 578 and maintained until O$_2$CON exceeds 22% at step 580, at which time control flow skips to step 582 and the next state is established (i.e. 75% oxygen concentration, see state "C" on FIG. 15).

With continuing reference to FIGS. 15 and 16b, to carry on from state "B" (step 556), the strategy of FIG. 16a is repeated, with the following changes: at step 540, an oxygen concentration of 36.5% is established; at stp 560, an oxygen concentration of 31% (state "D") is established; and at step 582, an oxygen concentration of 41.5 (state "E") is established. Similarly, to carry on from state "C" (step 582), the strategy of FIG. 16a is repeated, with the following changes: at step 540, an oxygen concentration of 75% is established; at step 560, an oxygen concentration of 62.5% (state "F") is established; and at step 582, an oxygen concentration of 87.5 (state "G") is established. Other ranges can be established by changing the oxygen saturation values in the condition boxes. Commonly used ranges might include 88%–92%, 90%–95%, 92%–97% and 95%–99%.

As shown in FIG. 16a, with control at step 544, if the condition of step 544 is positively answered, control goes to step 546. For every minimal oxygen state (i.e. 23.% oxygen concentration), there are a number of previous steps, analogous to FIG. 13b, connected in series and parallel by the rules of Mode Y, described in greater detail above. Two conditions ahead of the condition stated in Mode Y and identical to step 548 and 550 preferably follow each step. If the answers to both conditions are "no", control passes to step 552. If the answers are "yes", it control flows down the sequence. It should be appreciated that the test conditions of FIGS. 16a–16b can easily be altered in the microprocessor, to allow for higher oxygen concentrations in the oxyhood and in the neonate by ignoring input from the oxygen analyzer. It should be mentioned that the rationale for the extreme interactions between steps in FIG. 16a and 16b is to ensure that oxygen Concentration considerations dominate over oxygen saturation considerations, ensuring that the oxygen concentration at the analyzer remains between 22% and 60%.

Figure 17:
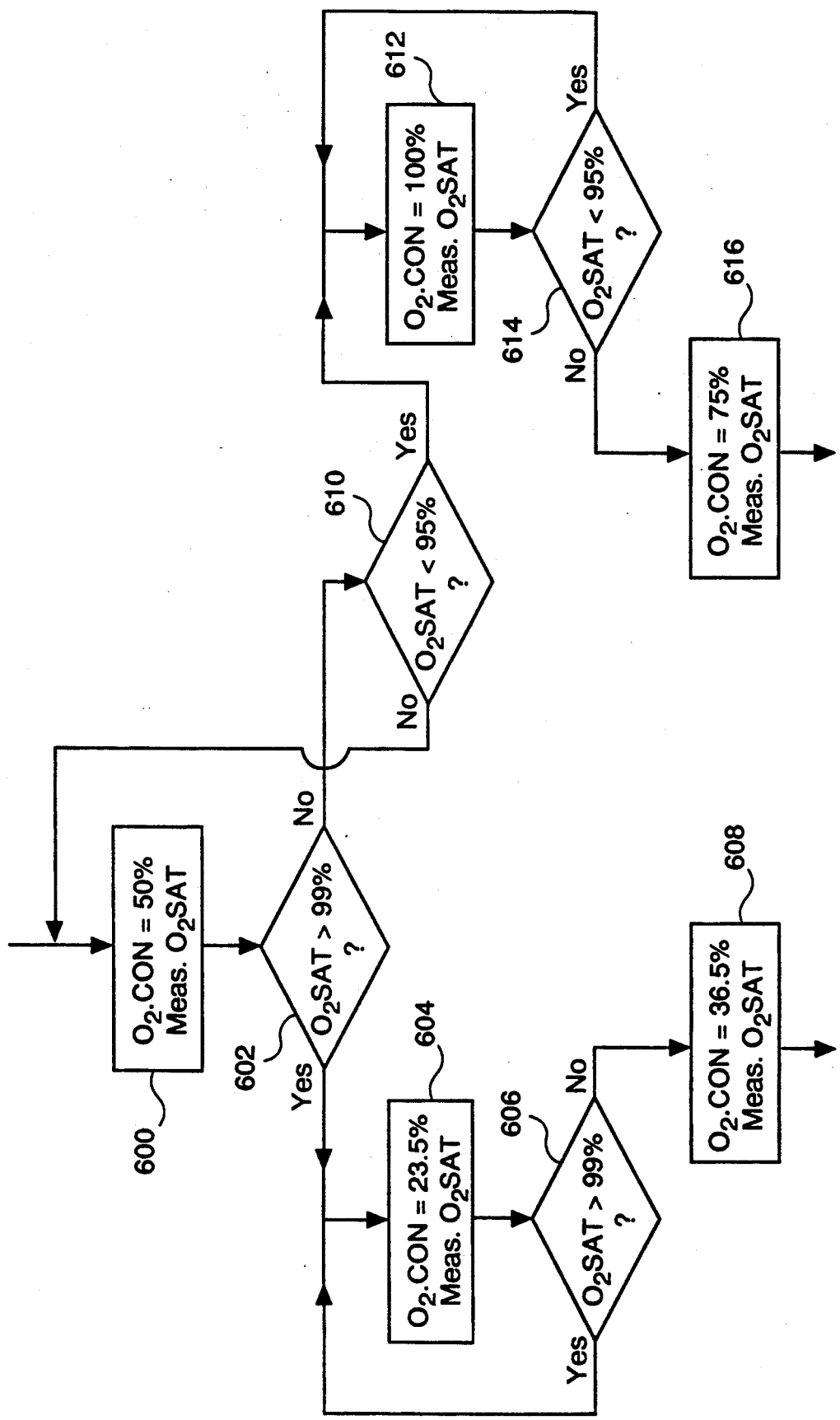
FIG. 17 is a flowchart detailing an oxygenation strategy for use with the neonatal oxyhood oxydosimeter shown in FIG. 15, wherein the oxygen saturation levels are maintained between 95% and 99%.

FIG. 17 is a flowchart illustrating an oxygenation strategy resulting in higher oxygen concentration in the oxyhood and higher oxygen saturation in the neonate, e.g. the desired range of oxygen saturation is 95%–99%, instead of 90%–95%. As shown in FIG. 17, at step 600 the microprocessor controls the valve to deliver oxygen to obtain a 50% concentration of oxygen in the oxyhood. After about five seconds the oxygen saturation of the neonate is measure and at step 602 the microprocessor determines whether the oxygen saturation ($O_2SAT$) is greater than 99%. If it is, at step 604 the microprocessor controls the valve to deliver oxygen to obtain a 23.5% concentration of oxygen in the oxyhood. Preferably, an oxygen concentration ($O_2CON$) of 23.5% is maintained by steps 604 and 606 until the oxygen saturation drops below 99%, at which point a 36.5% oxygen concentration is established, at step 608.

With continuing reference to FIG. 17, if the oxygen saturation was not greater than 99% at step 602, control flow skips to step 610, wherein the microprocessor determines whether $O_2SAT$ is below 95%. If it is not, the oxygen saturation is between 95% and 99%, as desired, and control flow returns to step 600. If, however, the oxygen saturation is below 95% at step 610, at step 612 the microprocessor controls the valve to obtain an oxygen concentration of 100% in the oxyhood. Preferably, an oxygen concentration of 100% is maintained by steps 612 and 614 until the oxygen saturation exceeds 95%, at which time the microprocessor appropriately controls the valve to obtain a 75% oxygen concentration in the oxyhood at step 616. To carry on from step 608, the strategy of FIG. 17 is repeated, with the following changes, as shown by the chart in FIG. 15: at step 600, an oxygen concentration of 36.5% is established; at step 608, an oxygen concentration of 31% is established; and at step 616 an oxygen concentration of 41.5% is established. Similarly, to carry on from step 616, the strategy of FIG. 17 is repeated, with the following changes, as shown by the chart in FIG. 15: at step 600, an oxygen concentration of 75% is established; at step 608, an oxygen concentration of 62.5% is established; and at step 616, an oxygen concentration of 87.5 is established. Still further, FIG. 17 could be altered to obtain a different range of acceptable oxygen saturation levels, e.g., 88%–92%, 90%–95%, and 92%–97%, just to name a few.

FULLY AUTOMATED RESPIRATOR

Figure 18:
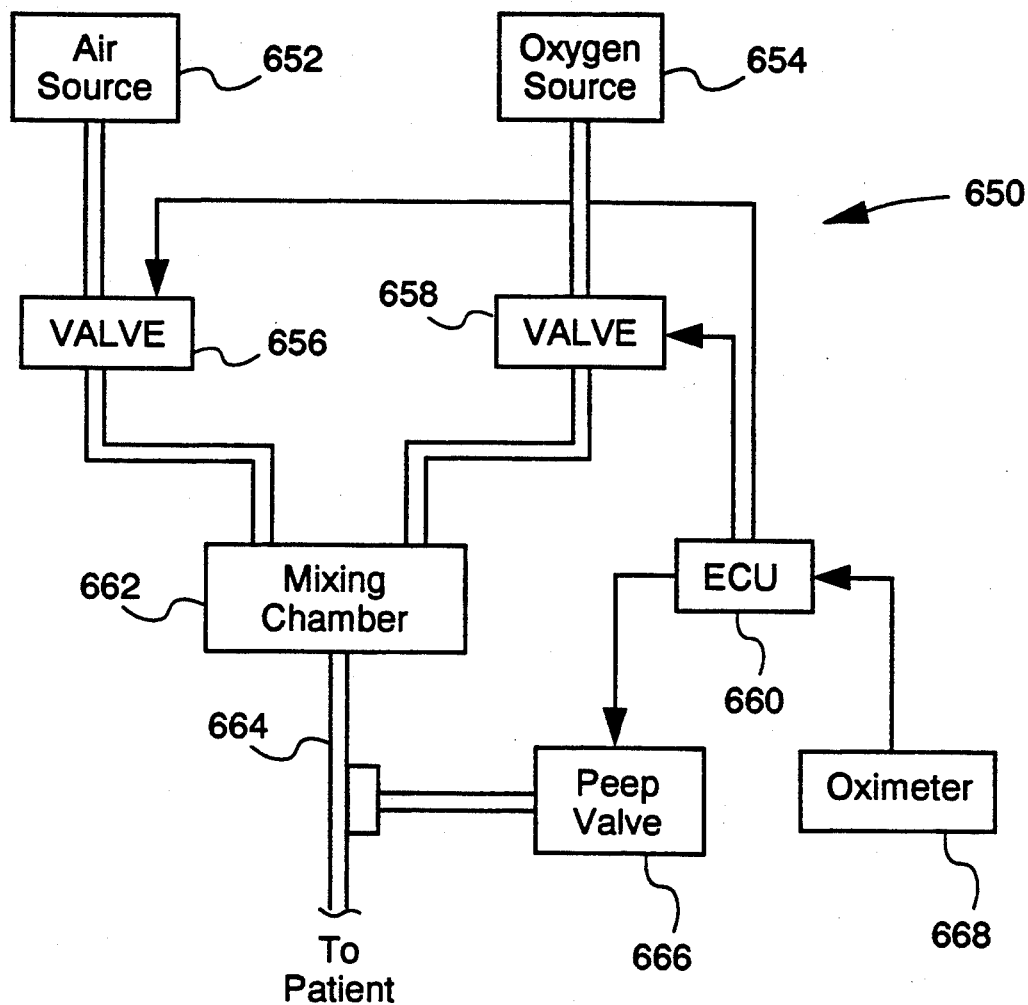
FIG. 18 is a block diagram of a fourth oxydosimeter embodiment of the present invention, for use as a fully automated respirator for oxygenation of adults and neonates.

Referring now to FIG. 18, there is shown a fourth oxydosimeter embodiment of the present invention shown generally by reference numeral 750, for use as a fully automated respirator. As illustrated, the fully automated respirator 650 includes a pressurized air source 652 and a pressurized oxygen source 654, both of which are in fluid communication with two complementary mixer valves 656 and 658, respectively. In the preferred embodiment, the valves 656 and 658 are variably opening twenty-nine increment solenoid valves with a coulomb controlling circuit, controlled by the ECU 670 according to the control strategy of the present invention, as described in greater detail below. By controlling the valves 656 and 658, varying amounts of air and oxygen are provided to a mixing chamber 662. Oxygen at varying concentrations is then output from the mixing chamber 662 and communicated to the tubing 664, which extends to the patient. This oxygen can be introduced to the patient utilizing an endotracheal tube or a nasal endotracheal tube, or the like. As illustrated, the oxydosimeter 650 also includes a positive and expiratory pressure (PEEP) valve 666 controlled by the ECU 660. The PEEP valve is a simple solenoid valve—not variably opening as are the complementary valves. The complementary mixer valves 656 and 658 and the PEEP valve 666 are controlled by the ECU based on data from the pulse oximeter 668. The PEEP valve 666 is intermittently controlled to provide an additional amount of pressurized oxygen to the patient as the patient exhales (expires) air from the lungs. Generally, the PEEP valve delivers 15 cm $H_2O$ to adults for all $O_2$ greater than 50%. For neonates, it delivers 6 cm $H_2O$ for all $O_2$ greater than 50%. Further differences will be shown later. Oxygen is delivered at varying concentrations to the patient to maintain an oxygen saturation level (always referring to the mean value with this device) within a predetermined range of acceptable values. Generally, the ECU controls the complementary mixer valves 656 and 658 and the PEEP valve 666 to deliver oxygen at varying concentrations to the patient to maintain a patient oxygen saturation level within a predetermined range of acceptable values.

Referring now to FIGS. 15, 11 and 12, there is shown a oxygenation chart and two flowcharts, detailing the oxygenation strategy of the present invention for use with fully automated respirate of FIG. 18, but with the following modifications. In FIG. 11, at step 400 replace the 1 L/min value with a 50% oxygen concentration value. At step 416, replace the 0.5 L/min value with 36.5% oxygen concentration. At step 412, replace the 1.5 L/min value with 75% oxygen concentration. This arrangement is shown in FIG. 17 if the oxygen saturation values in the condition boxes are changed as follows: replace 95 with 90 and 99 with 95. FIG. 17 will not be used, however, due to the similarities between the fully automated respirator and the flow sheets of the nasal prong oxydosimeter, previously described. In FIG. 12, at step 600, replace the 0.5 L/min value with 36.5% oxygen concentration. At step 432, replace the 0.25 L/min value with 31% oxygen concentration. At step 428, replace the 0.75 L/min value with 41.5% oxygen concentration.

As best shown with the above changes made to FIG. 11, at step 400, the ECU controls the solenoid valves 656 and 658 to obtain 50% oxygen saturation in the mixing chamber 662. The ECU also controls the PEEP valve to provide 15 cm of water for adults or 6 cm for neonates. In general, the PEEP valve is activated during states of greater oxygen concentration than 50%. In this device, all states last about five seconds.

Referring now to FIG. 15, there is shown a graphical representation of an oxygenation chart for use with the fully automated respirator shown in FIG. 18. In the preferred embodiment, each number represents an oxygen state defining the oxygen concentration in percent. After about five seconds at a particular state, the microprocessor measures the oxygen saturation of the neonate using a pulse oximeter. The relative direction of movement within the chart to the next state depends on the measured oxygen saturation. For example, in the preferred embodiment, if the measured oxygen saturation is a lower value, the next state is generally toward the right side of the chart, which corresponds to higher oxygen delivery rates. If, however, the oxygen saturation is a higher value, the next state is generally toward the left side of the chart, which corresponds to lower oxygen delivery rates.

With combined reference to FIGS. 11 and 15, at step 400, the microprocessor initially controls the valve to deliver oxygen at 50% concentration and after five seconds measures the oxygen saturation associated with that oxygen concentration. At step 402, the microprocessor determines whether the oxygen saturation of the patient is greater than 95%. If it is, the microprocessor adjusts the oxygen dosage to 23.5% oxygen concentration. If not, control passes to step 406. At step 402, the microprocessor determines whether the oxygen saturation ($O_2SAT_{50}$) of the patient is greater than 95%. If it is, the microprocessor adjusts the oxygen dosage reducing it to 23.5%, the lowest concentration at step 404 until the oxygen saturation level drops below 95%. If $O_2SAT_{50}$ is less than 95%, at step 406 the microprocessor determines whether $O_2SAT_{30}$ is less than 90%. If the oxygen saturation is not less than 90% at step 406 (i.e. between 90% and 95%), control flow returns to the previously mentioned sequence leading to step 400 wherein 50% oxygen concentration is delivered. If the oxygen saturation is less than 90%, the microprocessor controls the valve to deliver an oxygen concentration of 100% at step 408 for about five seconds, after which the microprocessor measures the new oxygen saturation ($O_2SAT_{100}$). At step 410, the microprocessor determines whether $O_2SAT_{100}$ is less than 90% and, if it is, control flow returns to step 408, wherein 100% oxygen concentration is delivered until the oxygen saturation exceeds 90%. If $O_2SAT_{100}$ is greater than 90%, the next state is established, wherein 75% oxygen concentration is delivered to the neonate at step 412. This state is indicated at point "C" in FIG. 15.

As shown in FIG. 11, after measuring the oxygen saturation associated with 23.5% oxygen concentration at step 404, the microprocessor again determines whether the oxygen saturation still exceeds 95% at step 414. If the oxygen saturation continues to be greater than 95%, control flow jumps back to step 404 such that a 23.5% oxygen concentration is delivered to the neonate. This process continues until the oxygen saturation drops below 95%, at which point the microprocessor controls the valve to deliver oxygen at 36.5% concentration at step 416 and measures the associated oxygen saturation ($O_2SAT_{36.5}$) after five seconds. This corresponds to state 36.5% oxygen concentration indicated at point "B" on FIG. 15.

To continue the strategy from step 416 and move along the chart of FIG. 15 from state 36.5% oxygen concentration to the next state, the flow chart of FIG. 11 is generally repeated as shown in FIG. 12. Thus, steps 416-432 are executed in the manner that steps 400-416 of FIG. 11 were executed to determine whether the next state is 31% (point "D" on FIG. 15) or 41.5% (point "E" on FIG. 15). That is, after oxygen has been delivered at 36.5% concentration for five seconds, the microprocessor determines whether $O_2SAT_{36.5}$ is greater than 95% at step 418. If it is, the microprocessor adjusts the oxygen dosage, reducing it to 23.5% concentration of oxygen, the lowest delivery concentration at step 420. If the oxygen saturation is less than 95%, at step 422, the microprocessor determines whether the oxygen saturation is less than 90%. If the oxygen saturation is less than 90%, the microprocessor controls the valve to deliver an oxygen concentration of 100% at step 424 for about five seconds, after which the microprocessor measures the new oxygen saturation ($O_2SAT_{100}$). If the oxygen saturation is not less than 90% at step 422, (i.e. between 90% and 95%), control flow returns to step 416 wherein 36.5% oxygen saturation is delivered. At step 426, the microprocessor determines whether $O_2SAT_{100}$ is less than 90% and, if it is, control flow returns to step 424 wherein 100% oxygen concentration is delivered until the oxygen saturation exceeds 90%. If $O_2SAT_{100}$ is greater than 90%, the next state is established and 41.5% oxygen concentration is delivered to the neonate at step 428.

As shown in FIG. 12, after measuring the oxygen saturation associated with 23.5% oxygen concentration at step 420, the microprocessor again determines whether the oxygen saturation still exceeds 95% at step 430. If the oxygen saturation continues to be greater than 95%, control flow jumps back to step 420 such that a dosage of 23.5% oxygen concentration continues until oxygen saturation drops below the 95% level, at which point a new state is established, and the microprocessor controls the valve to deliver oxygen at a concentration of 31% at step 432 and measures the associated oxygen saturation after five seconds.

In another embodiment of the present invention, the fully automated respirator has a plurality of operating modes. The above mode is suitable for adults and neonates. At the apical 50% $O_2$ concentration state in FIG. 11, there are eleven steps (not specifically illustrated for ease of illustration and sake of clarity) above step 400 and are identical to step 400. Between each step is a condition box to determine whether the oxygen saturation is greater than 95%. If it is, go to step 404. If not, go down the cascade and follow FIG. 11. For example, instead of maintaining oxygen saturation between 90% and 95%, as previously described, the fully automated respirator can function to maintain oxygen saturation between 88% and 92%, between 95% and 99%, or between 92% and 97%. These changes are easily made without changing the entire program or the hardware, and, except for these changes, the control strategy remains the same. It should be appreciated that this feature allows therapists and physicians to change the oxygen saturation range to any clinically useful range. Mode X and Mode Y apply to every maximum and minimum oxygen state as before.

For every maximal oxygen state, as before, steps analogous to FIG. 13b are connected in series and parallel, as discussed in greater detail above with reference to Mode X. Also, a condition identical to step 14 follows each step. If the answer to the condition is yes, control passes down the sequence. If no, control passes to step 412.

For every minimal oxygen state, there are a number of previous steps, analogous to FIG. 13b, connected in series and parallel, as discussed in greater above with reference to Mode Y. Also, a condition identical to step 414 follows each step. If the answer to the condition is yes, control passes down the sequence. If no, control passes to step 416.

It is understood, of course, that while the forms of the invention herein shown and described constitute the preferred embodiments of the invention, they are not intended to illustrate all possible forms thereof. It will also be understood that the words used are words of description rather than of limitation, and that various changes may be made without departing from the spirit and scope of the invention.

What is claimed is:

1. A method for delivering incremental doses of oxygen to a patient having an obstructive pulmonary disease to maximize the blood oxygen saturation level in the patient, the method comprising:
   (a) providing an oxydosimeter system including an electronic control unit (ECU) having memory, a pulse oximeter attached to a patient for measuring the oxygen saturation of the patient, and a plurality of valves controlled by the ECU for delivering oxygen to the patient;
   (b) energizing one of the plurality of valves to deliver the incremental doses of oxygen to the patient at a first rate;
   (c) measuring an associated average oxygen saturation level of the patient to obtain a first average oxygen saturation signal;
   (d) deenergizing the one valve and energizing another valve to deliver the incremental doses of oxygen to the patient at a second rate;
   (e) measuring a second average oxygen saturation level of the patient to obtain a second average oxygen saturation signal;
   (f) identifying a dominant valve based on the first average oxygen saturation signal and the second average oxygen saturation signal, the dominant valve being the valve associated with the higher average oxygen saturation level in the patient; and
   (g) energizing the dominant valve, thereby delivering the incremental doses of oxygen to the patient to maximize the blood oxygen saturation level in the patient.

2. The method of claim 1 further comprising:
   (h) establishing a baseline average oxygen saturation level based on the first average oxygen saturation signal and a predetermined number of previous average oxygen saturation levels stored in the memory; and
   (i) repeating steps (a)–(h) utilizing the dominant valve and another of the plurality of valves, the step of deenergizing occurring only if the first oxygen saturation level is within a predetermined range of the baseline average oxygen saturation level.

3. The method of claim 2 further comprising:
   (j) energizing an oxygen saturation exercise valve if the first average oxygen saturation level is outside of a predetermined range of the baseline average oxygen saturation levels, the oxygen saturation exercise valve delivering the maximum amount of oxygen to the patient for a predetermined amount of time.

* * * * *